US011577022B2

(12) United States Patent
Cowan et al.

(10) Patent No.: US 11,577,022 B2
(45) Date of Patent: Feb. 14, 2023

(54) SELF-ORIENTING SYRINGE AND SYRINGE INTERFACE

(71) Applicant: BAYER HEALTHCARE LLC, Whippany, NJ (US)

(72) Inventors: Kevin Cowan, Allison Park, PA (US); Barry Tucker, Verona, PA (US); Arthur Uber, III, Pittsburgh, PA (US); Edward Rhinehart, Murrysville, PA (US); James Neill, Oakdale, PA (US); Glen Williams, Springdale, PA (US); Michael Spohn, Fenelton, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 543 days.

(21) Appl. No.: 16/713,335

(22) Filed: Dec. 13, 2019

(65) Prior Publication Data
US 2020/0114065 A1  Apr. 16, 2020

Related U.S. Application Data

(63) Continuation of application No. 14/953,867, filed on Nov. 30, 2015, now Pat. No. 10,512,720, which is a
(Continued)

(51) Int. Cl.
*A61M 5/145* (2006.01)
*A61M 5/14* (2006.01)
*A61M 5/00* (2006.01)

(52) U.S. Cl.
CPC .......... *A61M 5/145* (2013.01); *A61M 5/1408* (2013.01); *A61M 5/14546* (2013.01);
(Continued)

(58) Field of Classification Search
CPC .......... A61M 5/14546; A61M 5/14566; A61M 5/1458
See application file for complete search history.

(56) References Cited

U.S. PATENT DOCUMENTS

| 1,591,761 A | 7/1926 | Haines |
| 1,988,480 A | 1/1935 | Campkin |

(Continued)

FOREIGN PATENT DOCUMENTS

| DE | 69507018 T2 | 8/1999 |
| DE | 69416686 T2 | 10/1999 |

(Continued)

*Primary Examiner* — Laura A Bouchelle
(74) *Attorney, Agent, or Firm* — Joseph L. Kent; David Schramm; James R. Stevenson

(57) ABSTRACT

A syringe includes a barrel having a distal end, a proximal end, and a sidewall extending therebetween along a longitudinal axis. At least one engagement member protrudes from a terminal portion of the sidewall in a proximal direction along the longitudinal axis. The at least one engagement member tapers axially in a direction from the distal end toward the proximal end. The at least one engagement member is configured for engagement with a locking mechanism of a fluid injector to releasably lock the syringe with the fluid injector. A taper of the at least one engagement member is configured to rotationally guide the syringe into alignment with the locking mechanism and axially eject the syringe upon rotation of the syringe. The locking mechanism operatively engages the at least one engagement member regardless of an orientation of the syringe about the longitudinal axis relative to the injector.

12 Claims, 13 Drawing Sheets

Related U.S. Application Data continuation of application No. 14/526,395, filed on Oct. 28, 2014, now Pat. No. 9,199,033.

(52) U.S. Cl.
CPC ......... *A61M 5/14566* (2013.01); *A61M 5/007* (2013.01); *A61M 2005/14573* (2013.01); *A61M 2205/19* (2013.01); *A61M 2205/6063* (2013.01)

(56) References Cited

U.S. PATENT DOCUMENTS

| | | | |
|---|---|---|---|
| 2,157,503 A | 5/1939 | Smith | |
| 2,627,720 A | 2/1953 | Williams et al. | |
| 2,734,504 A | 2/1956 | Crescas et al. | |
| 2,946,331 A | 7/1960 | Jungst et al. | |
| 2,956,563 A | 10/1960 | Sarnoff | |
| 3,115,135 A | 12/1963 | Sarnoff | |
| 3,348,545 A | 10/1967 | Sarnoff et al. | |
| 3,395,704 A | 8/1968 | Frey et al. | |
| 3,631,847 A | 1/1972 | Hobbs | |
| 3,701,345 A | 10/1972 | Heilman | |
| 3,738,539 A | 6/1973 | Beich | |
| 3,752,145 A | 8/1973 | Runnells et al. | |
| 3,812,843 A | 5/1974 | Wootten et al. | |
| 3,880,138 A | 4/1975 | Wootten et al. | |
| 4,006,736 A | 2/1977 | Kranys et al. | |
| 4,150,672 A | 4/1979 | Martin et al. | |
| 4,267,836 A | 5/1981 | Whitney et al. | |
| 4,269,185 A | 5/1981 | Whitney et al. | |
| 4,273,122 A | 6/1981 | Whitney et al. | |
| 4,342,312 A | 8/1982 | Whitney et al. | |
| 4,345,595 A | 8/1982 | Whitney et al. | |
| 4,351,335 A | 9/1982 | Whitney et al. | |
| 4,405,318 A | 9/1983 | Whitney et al. | |
| 4,424,720 A | 1/1984 | Bucchianeri | |
| 4,465,473 A | 8/1984 | Ruegg | |
| 4,573,978 A | 3/1986 | Reilly | |
| 4,634,431 A | 1/1987 | Whitney et al. | |
| 4,636,198 A | 1/1987 | Stade | |
| 4,677,980 A | 7/1987 | Reilly et al. | |
| 4,695,271 A | 9/1987 | Goethel | |
| 4,744,786 A | 5/1988 | Hooven | |
| 4,753,638 A | 6/1988 | Peters | |
| 4,854,324 A | 8/1989 | Hirschman et al. | |
| 4,869,720 A | 9/1989 | Chernack | |
| 4,936,833 A | 6/1990 | Sams | |
| 4,966,601 A | 10/1990 | Draenert | |
| 5,002,538 A | 3/1991 | Johnson | |
| 5,007,904 A | 4/1991 | Densmore et al. | |
| 5,098,386 A | 3/1992 | Smith | |
| 5,178,609 A | 1/1993 | Ishikawa | |
| 5,209,731 A | 5/1993 | Sterman et al. | |
| 5,219,099 A | 6/1993 | Spence et al. | |
| 5,269,762 A | 12/1993 | Armbruster et al. | |
| 5,279,569 A | 1/1994 | Neer et al. | |
| 5,300,031 A | 4/1994 | Neer et al. | |
| 5,383,858 A | 1/1995 | Reilly et al. | |
| 5,451,221 A | 9/1995 | Cho et al. | |
| 5,456,669 A | 10/1995 | Neer et al. | |
| 5,520,653 A | 5/1996 | Reilly et al. | |
| 5,535,746 A | 7/1996 | Hoover et al. | |
| 5,779,675 A | 7/1998 | Reilly et al. | |
| 5,782,815 A | 7/1998 | Yanai et al. | |
| 5,792,102 A | 8/1998 | Mueller-Spaeth | |
| 5,848,993 A | 12/1998 | Tanhehco et al. | |
| 5,873,861 A | 2/1999 | Hitchins et al. | |
| 5,944,694 A | 8/1999 | Hitchins et al. | |
| 5,947,929 A | 9/1999 | Trull | |
| 5,947,935 A | 9/1999 | Kazousky et al. | |
| 6,315,758 B1 | 11/2001 | Neer et al. | |
| 6,336,913 B1 | 1/2002 | Spohn et al. | |
| 6,368,307 B1 | 4/2002 | Ziemba et al. | |
| 6,432,089 B1 | 8/2002 | Kakimi et al. | |
| 6,520,930 B2 | 2/2003 | Critchlow et al. | |
| 6,620,134 B1 | 9/2003 | Trombley, III et al. | |
| 6,652,489 B2 | 11/2003 | Trocki et al. | |
| 6,659,979 B2 | 12/2003 | Neer et al. | |
| 6,716,195 B2 | 4/2004 | Nolan et al. | |
| 6,733,477 B2 | 5/2004 | Cowan et al. | |
| 6,743,202 B2 | 6/2004 | Hirschman et al. | |
| 6,808,507 B2 | 10/2004 | Roser | |
| 6,958,053 B1 | 10/2005 | Reilly | |
| 7,273,477 B2 | 9/2007 | Spohn et al. | |
| 7,361,156 B2 | 4/2008 | Joyce et al. | |
| 7,393,341 B2 | 7/2008 | Nemoto | |
| 7,419,478 B1 | 9/2008 | Reilly et al. | |
| 7,462,166 B2 | 12/2008 | Kowan et al. | |
| 7,497,843 B1 | 3/2009 | Castillo et al. | |
| 7,553,294 B2 | 6/2009 | Lazzaro et al. | |
| 7,563,249 B2 | 7/2009 | Schriver et al. | |
| 7,666,169 B2 * | 2/2010 | Cowan ................ A61M 5/007 604/151 |
| 7,674,244 B2 | 3/2010 | Kalafut et al. | |
| 7,682,345 B2 | 3/2010 | Savage | |
| 7,691,085 B2 | 4/2010 | Dedig et al. | |
| 7,846,136 B2 | 12/2010 | Witowski | |
| 3,012,125 A1 | 9/2011 | Fago et al. | |
| 8,038,651 B2 | 10/2011 | Keller | |
| 8,133,203 B2 | 3/2012 | Hack et al. | |
| 8,366,670 B2 | 2/2013 | Neer et al. | |
| 8,439,876 B2 | 5/2013 | Spohn et al. | |
| 8,572,834 B2 | 11/2013 | Cude | |
| 8,632,506 B2 | 1/2014 | Steenfeldt-Jensen et al. | |
| 8,721,596 B2 | 5/2014 | Trocki et al. | |
| 9,078,966 B2 | 7/2015 | Bruce | |
| 9,173,995 B1 | 11/2015 | Tucker et al. | |
| 9,199,033 B1 * | 12/2015 | Cowan ............ A61M 5/14546 | |
| 9,474,857 B2 | 10/2016 | Riley et al. | |
| 9,597,706 B2 | 3/2017 | Burns | |
| 9,700,670 B2 | 7/2017 | Tucker et al. | |
| 10,512,720 B2 * | 12/2019 | Cowan ............ A61M 5/14546 | |
| 2001/0047153 A1 | 11/2001 | Trocki et al. | |
| 2001/0047162 A1 | 11/2001 | Yugari | |
| 2002/0128607 A1 | 9/2002 | Haury et al. | |
| 2004/0064041 A1 | 4/2004 | Lazzaro et al. | |
| 2004/0122370 A1 | 6/2004 | Joyce et al. | |
| 2005/0171477 A1 | 8/2005 | Rubin et al. | |
| 2007/0219508 A1 | 9/2007 | Bisegna et al. | |
| 2008/0035234 A1 | 2/2008 | Khan et al. | |
| 2009/0112087 A1 | 4/2009 | Fago | |
| 2011/0106015 A1 | 5/2011 | Liscio et al. | |
| 2011/0208123 A1 | 8/2011 | Gray et al. | |
| 2012/0016234 A1 | 1/2012 | Nemoto et al. | |
| 2012/0265143 A1 | 10/2012 | Krumme et al. | |
| 2013/0274655 A1 | 10/2013 | Jennings et al. | |
| 2013/0281940 A1 | 10/2013 | Gelblum et al. | |
| 2013/0340608 A1 | 12/2013 | Yamamoto | |
| 2016/0114099 A1 | 4/2016 | Tucker et al. | |
| 2016/0354537 A1 | 12/2016 | Jozwik et al. | |

FOREIGN PATENT DOCUMENTS

| | | |
|---|---|---|
| DE | 69527281 T2 | 1/2003 |
| DE | 202004005433 U1 | 7/2004 |
| DE | 102004032970 A1 | 2/2006 |
| EP | 0143895 A1 | 6/1985 |
| EP | 0346950 A2 | 12/1989 |
| EP | 0362484 A2 | 4/1990 |
| EP | 0482677 B1 | 4/1998 |
| EP | 0893133 B1 | 11/2002 |
| EP | 1416994 A1 | 5/2004 |
| EP | 1188669 B1 | 8/2004 |
| EP | 1465101 A2 | 10/2004 |
| EP | 1281408 B1 | 11/2004 |
| EP | 1484071 A1 | 12/2004 |
| EP | 1512423 A1 | 3/2005 |
| EP | 1531889 A1 | 5/2005 |
| EP | 1563859 A1 | 8/2005 |
| EP | 1588728 A1 | 10/2005 |
| EP | 1596908 A1 | 11/2005 |
| EP | 1642606 A1 | 4/2006 |
| EP | 1647291 A1 | 4/2006 |
| EP | 1681069 A1 | 7/2006 |

(56) References Cited

FOREIGN PATENT DOCUMENTS

| | | |
|---|---|---|
| EP | 1688157 A1 | 8/2006 |
| EP | 1703924 A1 | 9/2006 |
| EP | 1723977 A1 | 11/2006 |
| EP | 1732093 A1 | 12/2006 |
| EP | 1736189 A1 | 12/2006 |
| EP | 1767233 A1 | 3/2007 |
| EP | 1782853 A1 | 5/2007 |
| EP | 1820523 A1 | 8/2007 |
| EP | 1820524 A1 | 8/2007 |
| EP | 1825875 A1 | 8/2007 |
| EP | 1825876 A1 | 8/2007 |
| EP | 1825877 A1 | 8/2007 |
| EP | 1827535 A2 | 9/2007 |
| EP | 1896100 A2 | 3/2008 |
| EP | 1932556 A1 | 6/2008 |
| EP | 1888218 B1 | 12/2008 |
| EP | 1486219 B1 | 4/2009 |
| EP | 2043708 A1 | 4/2009 |
| EP | 2015800 A4 | 5/2009 |
| EP | 2055332 A1 | 5/2009 |
| EP | 1847285 B1 | 9/2009 |
| EP | 1670522 B1 | 11/2009 |
| EP | 2156857 A2 | 2/2010 |
| EP | 2187993 A1 | 5/2010 |
| EP | 2227274 A1 | 9/2010 |
| EP | 2227276 A1 | 9/2010 |
| EP | 2240219 A2 | 10/2010 |
| EP | 2244766 A1 | 11/2010 |
| EP | 2253348 A1 | 11/2010 |
| EP | 2315148 A1 | 4/2011 |
| EP | 2025356 B1 | 5/2011 |
| EP | 2318966 A2 | 5/2011 |
| EP | 2331175 A1 | 6/2011 |
| EP | 2341456 A1 | 7/2011 |
| EP | 2347359 A2 | 7/2011 |
| EP | 2353118 A1 | 8/2011 |
| EP | 2361647 A1 | 8/2011 |
| EP | 2362791 A2 | 9/2011 |
| EP | 2376146 A2 | 10/2011 |
| EP | 2384778 A1 | 11/2011 |
| EP | 2409720 A1 | 1/2012 |
| EP | 2411071 A1 | 2/2012 |
| EP | 2416821 A1 | 2/2012 |
| EP | 2427234 A1 | 3/2012 |
| EP | 2429614 A2 | 3/2012 |
| EP | 2227275 B1 | 6/2012 |
| EP | 2464402 A2 | 6/2012 |
| EP | 2337595 B1 | 7/2012 |
| EP | 2481430 A1 | 8/2012 |
| EP | 2485790 A1 | 8/2012 |
| EP | 2316509 B1 | 10/2012 |
| EP | 2363158 B1 | 11/2012 |
| EP | 2536449 A1 | 12/2012 |
| EP | 1938853 B1 | 1/2013 |
| EP | 2222358 B1 | 1/2013 |
| EP | 2275155 B1 | 4/2013 |
| EP | 2316507 B1 | 4/2013 |
| EP | 2316506 B1 | 5/2013 |
| EP | 2359883 B1 | 5/2013 |
| EP | 2229199 B1 | 6/2013 |
| EP | 2416824 B1 | 6/2013 |
| EP | 2618870 A2 | 7/2013 |
| EP | 2621553 A2 | 8/2013 |
| EP | 2628496 A1 | 8/2013 |
| EP | 2363160 B1 | 9/2013 |
| EP | 2251053 B1 | 10/2013 |
| EP | 2643035 A2 | 10/2013 |
| EP | 2654843 A1 | 10/2013 |
| EP | 2665501 A1 | 11/2013 |
| EP | 1716884 B1 | 12/2013 |
| EP | 2286855 B1 | 12/2013 |
| EP | 2520318 B1 | 12/2013 |
| EP | 2671603 A1 | 12/2013 |
| EP | 2686040 A1 | 1/2014 |
| EP | 2692375 A1 | 2/2014 |
| EP | 2185227 B1 | 3/2014 |
| EP | 2707824 A2 | 3/2014 |
| EP | 2732393 A2 | 5/2014 |
| EP | 2734253 A1 | 5/2014 |
| GB | 848204 A | 9/1960 |
| GB | 1049263 A | 11/1966 |
| GB | 1576733 A | 10/1980 |
| GB | 2486690 A | 6/2012 |
| GB | 2501897 A | 11/2013 |
| JP | 2006512106 A | 4/2006 |
| JP | 2009540995 A | 11/2009 |
| JP | 2010214048 A | 9/2010 |
| JP | 4833984 B2 | 12/2011 |
| JP | 2012106029 A | 6/2012 |
| JP | 2012120934 A | 6/2012 |
| JP | 4965582 B2 | 7/2012 |
| JP | 2014004480 A | 1/2014 |
| JP | 5436897 B2 | 3/2014 |
| JP | 5518844 B2 | 6/2014 |
| WO | 0012157 A1 | 3/2000 |
| WO | 0012158 A1 | 3/2000 |
| WO | 2004004812 A1 | 1/2004 |
| WO | 2007130061 A1 | 11/2007 |
| WO | 2008009645 A1 | 1/2008 |
| WO | 2009036496 A2 | 3/2009 |
| WO | 2011131778 A1 | 10/2011 |
| WO | 2011131783 A2 | 10/2011 |
| WO | 2012124028 A1 | 9/2012 |
| WO | 2012155035 A1 | 11/2012 |
| WO | 2013149979 A1 | 10/2013 |

* cited by examiner

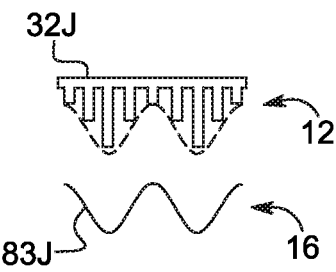 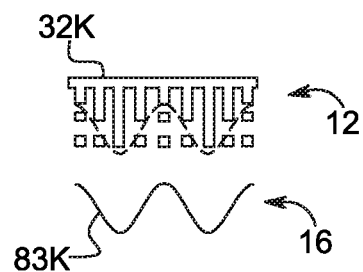 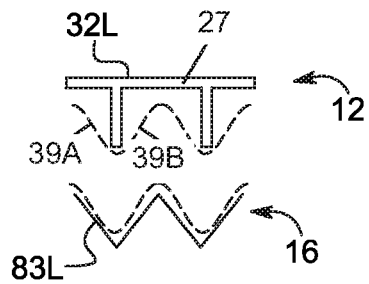
FIG. 4J   FIG. 4K   FIG. 4L
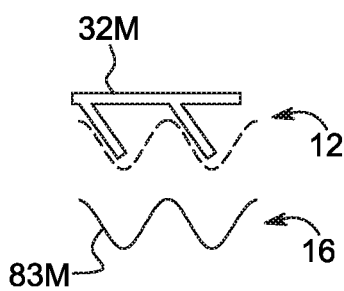 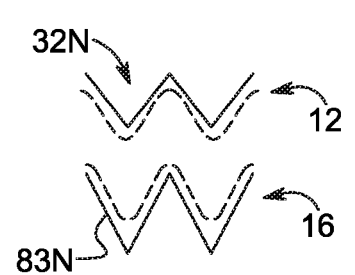 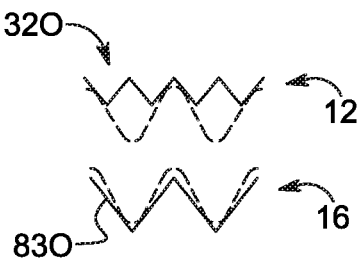
FIG. 4M   FIG. 4N   FIG. 4O
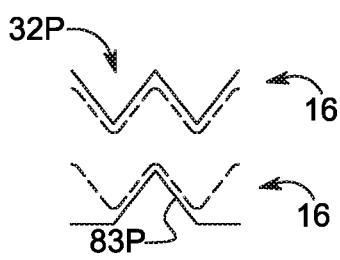 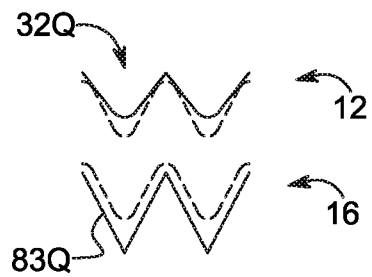
FIG. 4P   FIG. 4Q

SELF-ORIENTING SYRINGE AND SYRINGE INTERFACE

CROSS REFERENCE TO RELATED APPLICATIONS

The present application is a continuation application of U.S. application Ser. No. 14/953,867, filed on Nov. 30, 2015, now U.S. Pat. No. 10,512,720, which is a continuation under 37 C.F.R § 1.53(b) and claims priority under 35 U.S.C. § 120 to U.S. application Ser. No. 14/526,395, filed Oct. 28, 2014, now U.S. Pat. No. 9,199,033, the disclosures of which are incorporated herein by this reference.

BACKGROUND

Field of the Disclosure

The present disclosure relates generally to a system including a self-orienting, front-loading syringe for use with a fluid injector and, further, to a connection interface for securing the syringe to the fluid injector and to a method for loading and removal of the syringe to and from the fluid injector.

Description of Related Art

In many medical diagnostic and therapeutic procedures, a medical practitioner, such as a physician, injects a patient with one or more medical fluids. In recent years, a number of injector-actuated syringes and fluid injectors for pressurized injection of medical fluids, such as a contrast solution (often referred to simply as "contrast"), a flushing agent, such as saline, and other medical fluids have been developed for use in procedures such as angiography, computed tomography (CT), ultrasound, magnetic resonance imaging (MRI), positron emission tomography (PET), and other molecular imaging procedures. In general, these fluid injectors are designed to deliver a preset amount of fluid at a preset pressure and/or flow rate.

In some injection procedures, the medical practitioner places a catheter or a needle connected to tubing, or other fluid delivery connection into a vein or artery of the patient. The catheter or the tubing is connected to either a manual or to an automatic fluid injection mechanism. Automatic fluid injection mechanisms typically include at least one syringe connected to at least one fluid injector having, for example, at least one powered linear piston. The at least one syringe includes, for example, a source of contrast and/or a source of flushing fluid. The medical practitioner enters settings into an electronic control system of the fluid injector for a fixed volume of contrast and/or saline and a fixed rate of injection for each.

The injected contrast and/or saline are delivered to a patient's vasculature through the catheter or needle inserted into the patient's body, such as the patient's arm or groin area. A dose of contrast is referred to as a bolus. Once the bolus of contrast is delivered to the desired site, that area is imaged using a conventional imaging technique, such as angiography imaging or scanning, computed tomography (CT), ultrasound, magnetic resonance imaging (MRI), positron emission tomography (PET), and other molecular imaging procedures. The presence of the contrast becomes clearly visible against the background of the surrounding tissue.

Various front-loading connection interfaces have been developed to facilitate the loading and removal of the syringe to and from the fluid injector. In some embodiments, the syringe having a retention feature is inserted into a syringe port on the fluid injector by aligning the syringe with a corresponding locking feature provided on the fluid injector. It is often necessary for the medical practitioner to manually align the retention feature of the syringe with the corresponding locking feature on the fluid injector before the syringe can be loaded onto the injector. In some cases, there are only one or two alignments, such as shown in U.S. Pat. No. 6,336,913. In this syringe, the operator must manually rotate the syringe to find an alignment that allows the syringe to engage the fluid injector. It is then necessary for the operator to manually rotate the syringe relative to the locking feature to create a strong enough engagement for operation of the injector. In another syringe disclosed in U.S. Pat. No. 6,652,489, there is no need to rotationally align the syringe or to rotate the syringe for installation or engagement. To remove the syringe, the operator must rotate the syringe at least 45 degrees, and more commonly 90 degrees, about its longitudinal axis to disengage the locking mechanism. After rotation, the operator must then physically pull the syringe out of the injector. In some embodiments, the operator must pull on the syringe at the same time while rotating the syringe. Such syringe injector features require additional time and effort to load/remove the syringe from the injector, resulting in increased time for a medical injection procedure.

Accordingly, there is a need in the art for an improved syringe and injector attachment, interface, and/or locking feature that allows the operator to more easily disengage or release the syringe from the fluid injector, for example to relieve the operator of the effort of simultaneously pulling and rotating the syringe. There is a further need in the art for reducing or eliminating the need for rotationally aligning the syringe with the fluid injector during installation of the syringe on the fluid injector. While various syringes, syringe connection interfaces and methods are known in the medical field, improved syringes, connection interfaces between the syringe and the fluid injector and methods for loading and removing the syringe to and from the fluid injector continue to be in demand.

SUMMARY OF DISCLOSURE

In view of certain disadvantages of the existing connection interfaces between the syringe and the fluid injector, there is a need in the art for an improved syringe and connection interface between the syringe and the fluid injector that overcomes the deficiencies of the prior art. There is an additional need for improved methods for loading or installing and removing the syringe to and from the fluid injector so that the syringe does not have to be rotationally aligned about its longitudinal axis relative to the fluid injector to allow loading or removal of the syringe to and from the fluid injector.

In one embodiment, a syringe may include a barrel having a distal end, a proximal end, and a substantially circumferential sidewall extending between the distal end and the proximal end along a longitudinal axis. At least one engagement member may protrude from a terminal portion at the proximal end of the sidewall in a proximal direction along the longitudinal axis. The at least one engagement member may taper axially and/or circumferentially in a direction from the distal end toward the proximal end. The at least one engagement member may be configured for engagement with a locking mechanism of a fluid injector to releasably position the syringe within a syringe port of the fluid injector. A taper of the at least one engagement member may be configured to rotationally guide the syringe into alignment with the locking mechanism and axially eject the syringe upon rotation of the syringe.

In another embodiment, a plurality of engagement members may extend about at least a portion of a circumference of the terminal portion. The plurality of engagement members may be spaced apart evenly or unevenly about the circumference of the terminal portion. In certain embodiments, the at least one engagement member may have a wave form or a substantially sinusoidal form. In other embodiments, the at least one engagement member may have a pointed proximal end with at least one tapered surface that extends from the pointed proximal end in a distal direction along the longitudinal axis to the terminal portion of the sidewall. The pointed proximal end of the at least one engagement member may have a sharp or rounded point. The at least one tapered surface may be angled relative to a direction of the longitudinal axis. The at least one tapered surface may be linear, curvilinear, continuous, discontinuous, or planar. In some embodiments, an encoding device may be provided on at least a portion of the syringe, such as on at least one of the at least one engagement member. In certain embodiments, the at least one engagement member may be monolithically formed with the terminal portion of the sidewall. The at least one engagement member may have a circular, triangular, or a polygonal shape. In other embodiments, the at least one engagement member may be separable from the terminal portion of the sidewall.

In another embodiment, a retention flange may protrude radially outwardly from the outer surface of the sidewall relative to the longitudinal axis and distally of the at least one engagement member for engaging with the locking mechanism of the fluid injector to releasably lock the syringe with the syringe port of the fluid injector. The retention flange may extend around at least a portion of the outer surface of the sidewall. The retention flange may interact with at least one deflectable retaining element to retain the syringe within the locking mechanism. In certain embodiments, the retention flange may have a longitudinal stop surface for limiting a length of a longitudinal insertion of the syringe into the locking mechanism. A plunger may be slidably disposed within the barrel of the syringe and movable between the proximal end and the distal end. The syringe may further include a drip flange distal to the retention flange for preventing medical fluid from dripping from the distal end of the syringe into a syringe port of a medical injector and fouling the interior workings of the medical injector.

In another embodiment, a fluid injection apparatus may include at least one syringe having a barrel with a distal end, a proximal end, and a substantially circumferential sidewall extending between the distal end and the proximal end along a longitudinal axis. The barrel may have at least one engagement member protruding from a terminal portion of the proximal end of the sidewall in a proximal direction along the longitudinal axis. The at least one engagement member may taper axially and/or circumferentially in a direction from the distal end toward the proximal end. The fluid injection apparatus may further include an injector having an injector housing defining at least one syringe port for receiving the proximal end of the at least one syringe. A locking mechanism may be associated with the at least one syringe port for releasably securing the at least one syringe within the at least one syringe port. The locking mechanism may be configured for engaging the at least one engagement member of the syringe to releasably position the at least one syringe. A taper of the at least one engagement member may be configured to rotationally guide the syringe into self-alignment with the locking mechanism and axially eject the syringe upon rotation of the syringe within the locking mechanism. In certain embodiments, rotation of the syringe within the locking mechanism disengages the retention flange from the at least one deflectable retaining element prior to axially ejecting the syringe.

In yet another embodiment, the locking mechanism may include a housing having a central opening configured to receive the proximal end of the at least one syringe. A guide ring may be fixed relative to the housing with a central axis of the guide ring in coaxial alignment with a central axis of the housing. The guide ring may have at least one recess extending from an inner circumference of the guide ring to an outer circumference of the guide ring. At least one deflectable retaining element may be configured to be movably received within the at least one recess of the guide ring. A lock/release ring may be configured for engagement with the at least one engagement member when the at least one syringe is inserted into the at least one syringe port. The lock/release ring may be rotatable relative to the housing with a rotation of the at least one syringe about the longitudinal axis. At least one elastically resilient member may be connected at one end to at least a portion of the at least one deflectable retaining element to urge the at least one deflectable retaining element in a radially inward direction to disengage a retention flange on the at least one syringe.

In another embodiment, the at least one deflectable retaining element may have a locking lip that is angled relative to the longitudinal axis such that movement of the at least one syringe in a proximal direction causes movement of the at least one deflectable retaining element in a radially outward direction. The lock/release ring may include one or more syringe engagement members that have a complementary shape to receive the at least one engagement member. The lock/release ring may include at least one guide slot disposed on a top surface to guide a movement of the at least one deflectable retaining element. The at least one guide slot may include at least one guide track. The at least one deflectable retaining element may engage the at least one guide track at a first end when the at least one deflectable retaining element is in a first radial position, and may engage the at least one guide track at a second end when the at least one deflectable retaining element is in a second radial position that is different than the first radial position. Lateral edges of the at least one recess may define a travel path for guiding movement of the at least one deflectable retaining element. At least a portion of a top surface of the guide ring may define a stop surface that limits a movement of the at least one syringe in a proximal direction when the at least one syringe is inserted into the at least one syringe port.

In a further embodiment, a syringe may include a barrel having a distal end, a proximal end, and a substantially circumferential sidewall extending between the distal end and the proximal end along a longitudinal axis. At least one engagement member may protrude from a terminal portion of the proximal end of the sidewall in a proximal direction along the longitudinal axis. The at least one engagement member may taper axially and/or circumferentially in a direction from the distal end toward the proximal end. A retention flange may protrude radially outwardly from the outer surface of the sidewall relative to the longitudinal axis and distally of the at least one engagement member. The at least one engagement member may be configured for engagement with a locking mechanism of a fluid injector to releasably position the syringe within the syringe port of the fluid injector. A taper of the at least one engagement member may be configured to rotationally guide the syringe into self-alignment with the locking mechanism and axially eject the syringe upon rotation of the syringe. In certain embodiments, rotation of the syringe within the locking mechanism disengages the retention flange from the at least one deflectable retaining element prior to axially ejecting the syringe.

These and other features and characteristics of the syringe and the syringe connection interface of the fluid injection apparatus, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only. As used in the specification and the claims, the singular form of "a", "an", and "the" include plural referents unless the context clearly dictates otherwise.

DETAILED DESCRIPTION OF THE PREFERRED EMBODIMENTS

Figure 1A:
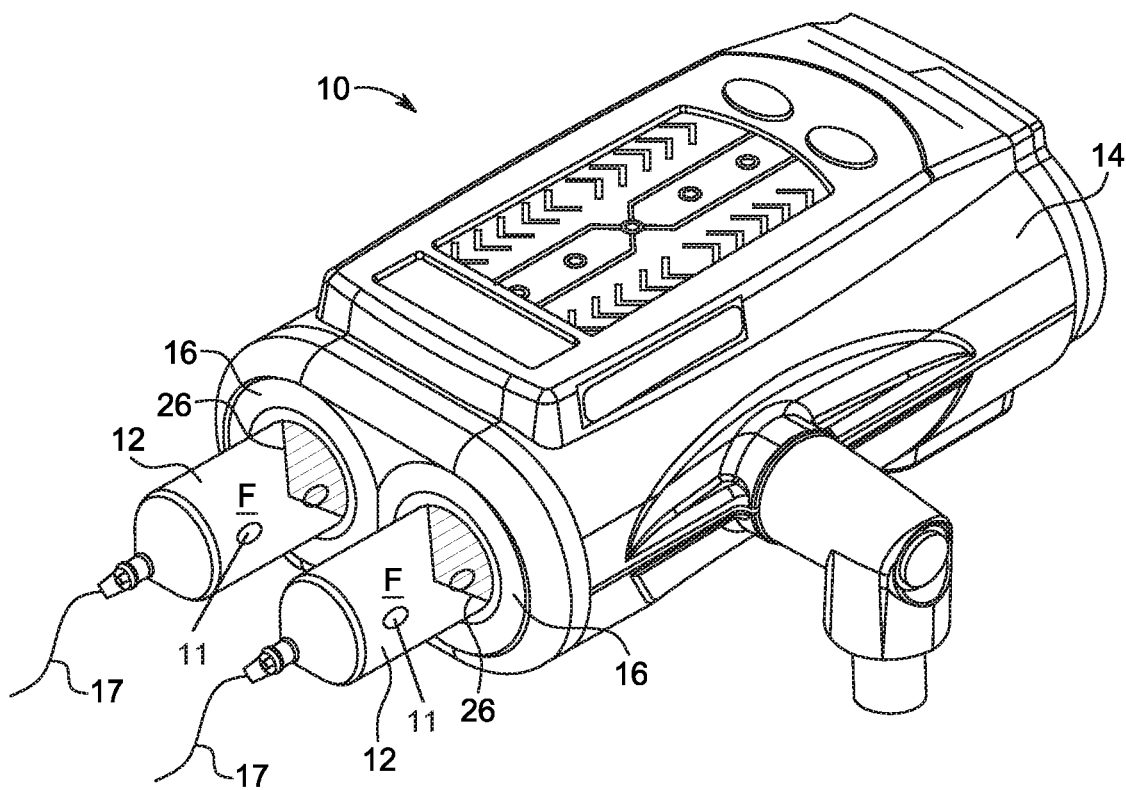
FIG. 1A is a schematic view of a system including a fluid injector and syringe according to an embodiment of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe, the term "proximal" refers to a portion of a syringe nearest to an injector when a syringe is oriented for connecting to an injector. The term "distal" refers to a portion of a syringe farthest away from an injector when a syringe is oriented for connecting to an injector. The term "radial" refers to a direction in a cross-sectional plane normal to a longitudinal axis of a syringe extending between proximal and distal ends. The term "circumferential" refers to a direction around an inner or outer surface of a sidewall of a syringe. The term "axial" refers to a direction along a longitudinal axis of a syringe extending between proximal and distal ends. The term "self-orienting" means that a syringe orients itself to the correct orientation within a syringe port during insertion without effort by a technician. The terms "axial taper", "axial tapering", and "tapering axially" mean an angle of inclination of at least one virtual or real surface on a syringe in a cylindrical plan projection view in a direction from a distal end toward a proximal end of a syringe. It is also to be understood that specific devices and processes illustrated in the attached drawings, and described in the following specification, are simply exemplary embodiments of the disclosure. Hence, specific dimensions and other physical characteristics related to the embodiments (i.e., aspects, variants, variations, etc.) disclosed herein are not to be considered as limiting.

Referring to the drawings in which like reference characters refer to like parts throughout the several views thereof, the present disclosure is generally directed to a connection interface between at least one syringe and a fluid injector.

With reference to FIG. 1A, a fluid injector 10 (hereinafter referred to as "injector 10"), such as an automated or powered fluid injector, is illustrated, which is adapted to interface with and actuate one or more syringes 12, which may be filled with a medical fluid F, such as contrast media, saline solution, or any desired medical fluid. The injector 10 may be used during a medical procedure to inject the medical fluid into the body of a patient by driving a plunger 26 of the syringe 12 with a piston element. The injector 10 may be a multi-syringe injector, wherein several syringes 12 may be oriented in a side-by-side or other relationship and are separately actuated by plungers 26 on respective linear actuators or piston elements associated with the injector 10. The injector 10 may be configured to independently deliver one or more fluids from the at least one syringes 12.

The injector 10 may be enclosed within a housing 14 formed from a suitable structural material, such as plastic or metal. The housing 14 may be of various shapes and sizes depending on the desired application. For example, the injector 10 may be a free-standing structure configured to be placed on the floor or may be a smaller design for placement on a suitable table or support frame. The injector 10 includes at least one syringe port 16 for connecting the at least one syringe 12 to respective piston elements. As will be described hereinafter, in some embodiments, the syringe 12 includes at least one engagement member configured for releasably self-orienting the syringe 12 within the syringe port 16 of the injector 10. The at least one engagement member is configured to operatively engage a locking mechanism provided in the syringe port 16 of the injector 10 to facilitate loading or removal of the syringe 12 to and from the injector 10, including ejecting the syringe 12 from the syringe port 16, as will be described herein. The at least one engagement member and the locking mechanism together define a connection interface for reversibly connecting the at least one syringe 12 to the injector 10.

A fluid path set 17 may be fluidly connected with at least one of the at least one syringe 12 for delivering medical fluid F from the at least one syringe 12 to a catheter (not shown), needle, or other fluid delivery connection inserted into a patient at a vascular access site. Fluid flow from the at least one syringe 12 may be regulated by a fluid control module (not shown). The fluid control module operates various pistons, valves and flow regulating structures to regulate the delivery of the medical fluid, such as saline solution and contrast to the patient based on user selected injection parameters, such as injection flow rate, duration, total injection volume, and ratio of contrast media and saline. A suitable front-loading fluid injector that may be modified for use with at least one syringe and at least one syringe interface for self-oriented loading and releasable retaining of the at least one syringe with the fluid injector described herein is disclosed in U.S. Pat. No. 5,383,858 to Reilly et al. which is incorporated by reference in its entirety. Other relevant multi-fluid delivery systems that may be so modified are found in U.S. Pat. No. 7,553,294 to Lazaro et al.; U.S. Pat. No. 7,666,169 to Cowan et al.; International Patent Application No. PCT/US2012/037491, (published as WO 2012/155035); and United States Patent Application Publication No. 2014/0027009 to Riley et al.; all of which are assigned to the assignee of the present application, and the disclosures of which are incorporated herein by reference.

Figure 1B:
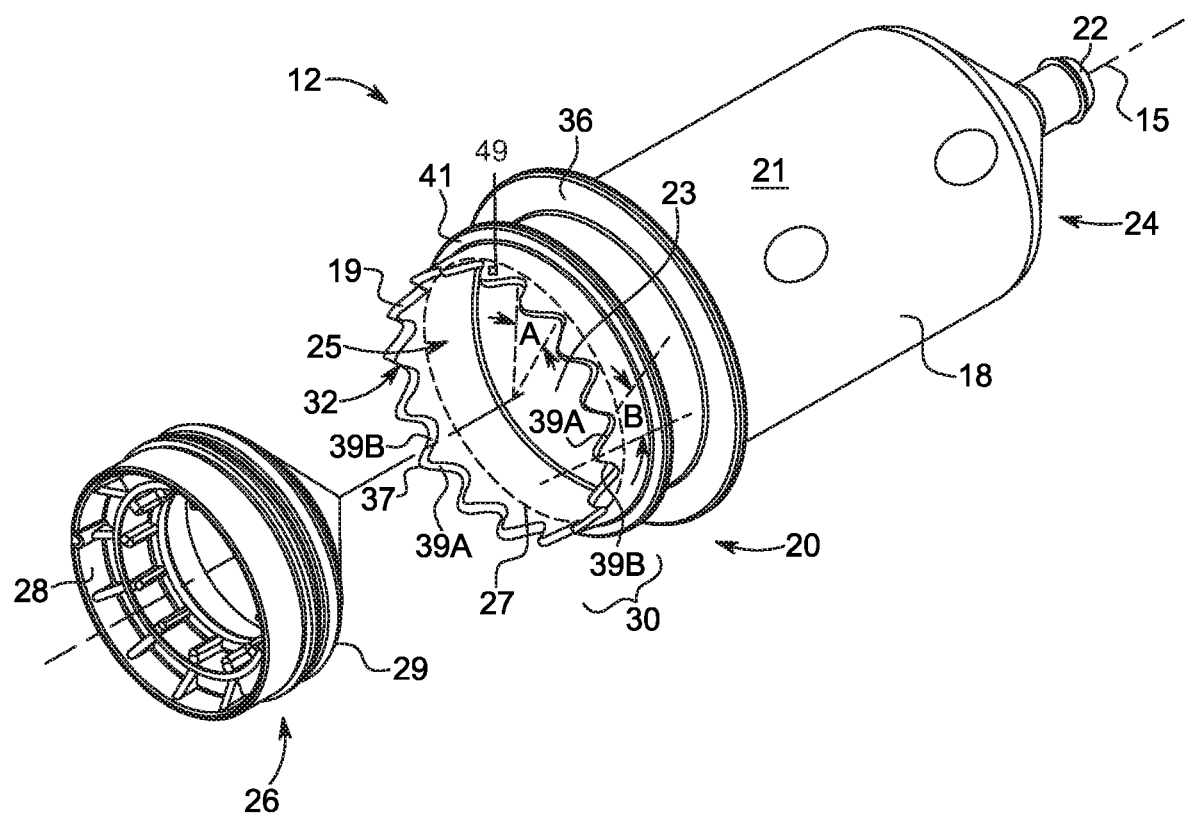
FIG. 1B is a perspective view of a syringe according to one embodiment of the present disclosure.

Having described the general structure and function of the injector 10, the structure of the at least one syringe 12 will now be discussed in greater detail. With reference to FIG. 1B, the syringe 12 generally has a substantially cylindrical syringe barrel 18 formed from glass, metal, or a suitable medical-grade plastic. The barrel 18 has a proximal end 20 and a distal end 24, with a substantially circumferential sidewall 19 extending therebetween along a length of a longitudinal axis 15 extending through a center of the barrel 18. The barrel 18 may be made from a transparent or translucent material, and may include at least one fluid verification member 11 for verifying a presence of the fluid F within the syringe barrel 18 (shown in FIG. 1A). A nozzle 22 for connecting to a fluid path 17 extends from the distal end 24 of the barrel 18. The barrel 18 has an outer surface 21 and an inner surface 23 that defines an interior volume 25 configured for receiving the medical fluid therein. The proximal end 20 of the barrel 18 may be sealed with the plunger 26 that is slidable through the barrel 18. The plunger 26 forms a liquid-tight seal against the inner surface of sidewall 19 of the barrel 18 as it is reversibly advanced therethrough. The plunger 26 may have a rigid inner element 28 configured for engagement with the piston of the injector 10. The plunger 26 may further include an elastomeric cover 29 disposed over at least a portion of the rigid inner element 28. The elastomeric cover 29 is configured to engage the inner surface 23 of the barrel 18 and provide a liquid-tight seal against the sidewall 19 of the barrel 18 as it is reversibly advanced therethrough.

With continued reference to FIG. 1B, the proximal end 20 of the syringe 12 is sized and adapted to be inserted in the at least one syringe port 16 of the injector 10 (shown in FIG. 1A). In some embodiments, the proximal end 20 of the syringe 12 defines an insertion portion 30 that is configured to be removably inserted into the syringe port 16 of the injector 10 while the remaining portion of the syringe 12 remains outside of the syringe port 16. As will be described in detail hereinafter, in certain embodiments, the proximal end 20 of the syringe 12 includes at least one engagement member 32 adapted to form a locking engagement with a corresponding locking mechanism in the syringe port 16 of the injector 10 for releasably retaining the syringe 12 in the syringe port 16. The combination of the syringe 12 having the one or more engagement members 32 with a retention flange 41 and the locking mechanism 35 (shown in FIG. 2B) of the injector 10 defines a connection interface for loading and unloading of the syringe 12 to and from the injector 10.

According to certain embodiments, a drip flange 36 may extend radially outward from the outer surface 21 of the syringe barrel 18 relative to the longitudinal axis 15. The drip flange 36 may extend around at least a portion of the outer circumference of the barrel 18. In one embodiment, the drip flange 36 is positioned distally along the longitudinal axis 15 relative to the one or more engagement members 32 and distal to the retention flange 41. The drip flange 36 may be configured to prevent fluid that drips from the nozzle 22 from entering the syringe port 16 on the injector 10. In this manner, the drip flange 36 helps reduce the amount of fluid that may enter the syringe port 16 and jam or interfere with the connection interface 100 or otherwise foul the mechanics or electronics of the injector 10. In some embodiments, the drip flange 36 may define an insertion stop surface that delimits how far the insertion portion 30 of the syringe 12 may be inserted into the syringe port 16 and/or locking mechanism of the injector 10. The drip flange 36 may be formed integrally with the barrel 18 or it may be affixed or otherwise secured to the outer surface 21 of the barrel 18 using, for example, a frictional fit and/or an adhesive, welding, or by molding. In other embodiments, the drip flange 36 may be formed on the outer surface 21 of the barrel 18 by etching, laser cutting, or machining.

In other embodiments, the insertion stop surface may be defined by the retention flange 41 positioned closer to the proximal end 20 of the barrel 18 relative to the drip flange 36, if present. The retention flange 41 may extend radially outward from the outer surface 21 of the syringe barrel 18 relative to the longitudinal axis 15. The retention flange 41 may extend around at least a portion of the outer circumference of the barrel 18 and may be a single continuous flange or one or more discontinuous or intermittent segments. In one embodiment, the retention flange 41 is positioned distally along the longitudinal axis 15 relative to the engagement member 32. The retention flange 41 may be formed integrally with the barrel 18 or it may be affixed or otherwise secured to the outer surface 21 of the barrel 18 using, for example, a frictional fit and/or an adhesive, welding, or by molding. In other embodiments, the retention flange 41 may be formed on the outer surface 21 of the barrel 18 by etching, laser cutting, or machining. The retention flange 41 may be anywhere along the length of the barrel 18 in a distal direction from the one or more engagement members 32. In some embodiments, the retention flange 41 may be formed directly on or adjacent the one or more engagement members 32. The retention flange 41 may also be formed by increasing the thickness of the sidewall 19 while maintaining a constant inner diameter of the barrel 18 or by increasing the inner diameter of the barrel 18 and maintaining, decreasing, or increasing the thickness of the sidewall 19. In this example embodiment, the distal surface of the retention flange 41 forms a retention surface 41R (shown in FIG. 2A) which interfaces with one or more retention surfaces 78R (shown in FIG. 2B) on one or more retaining elements 78 of syringe port 16. At least a portion of the retention flange 41, for example a proximal surface of retention flange 41, may be tapered or beveled in a radial direction toward or away from the longitudinal axis 15.

Figure 2A:
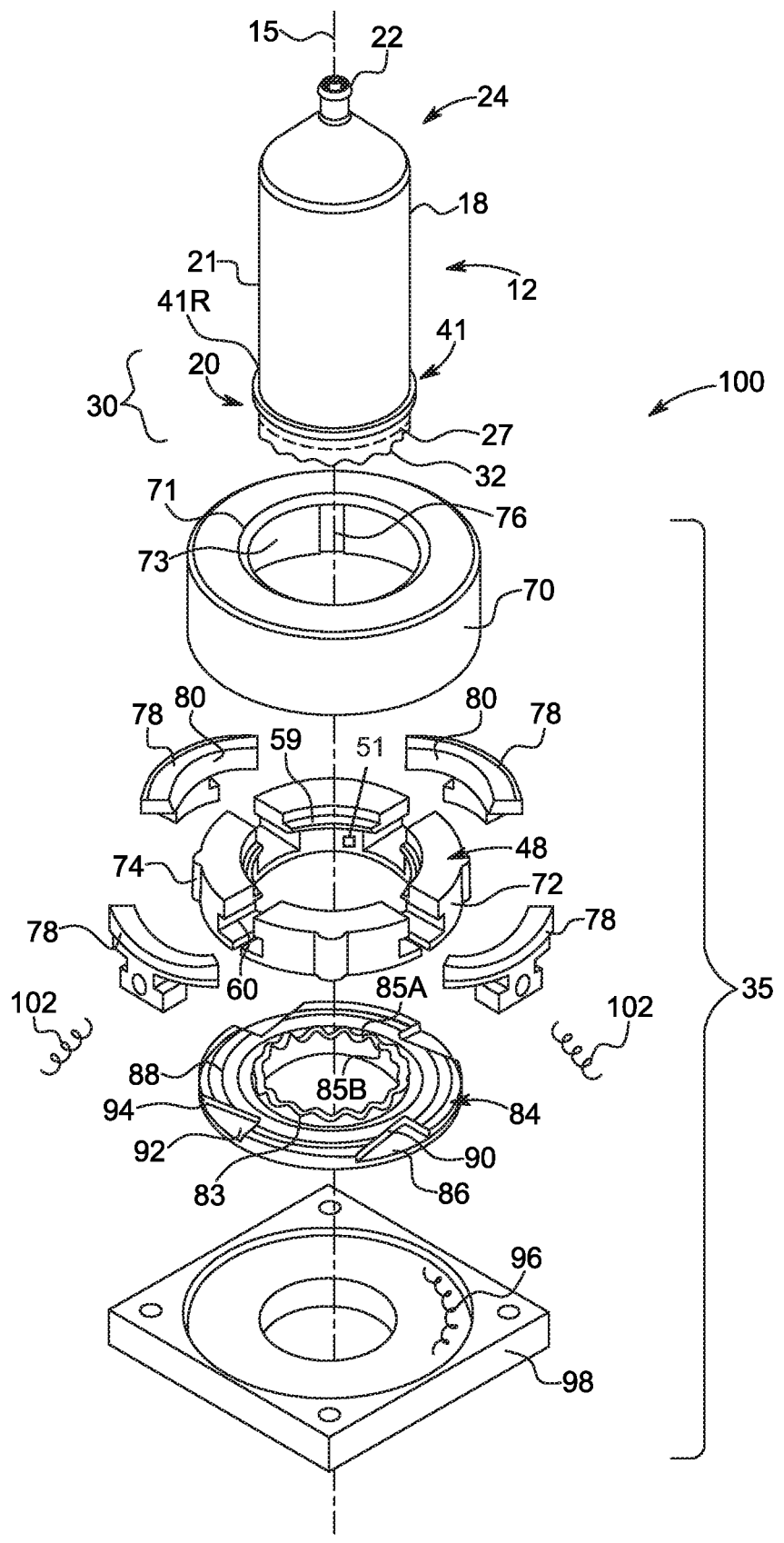
FIG. 2A is an exploded perspective view of a connection interface for securing a syringe to a fluid injector according to one embodiment.
Figure 2B:
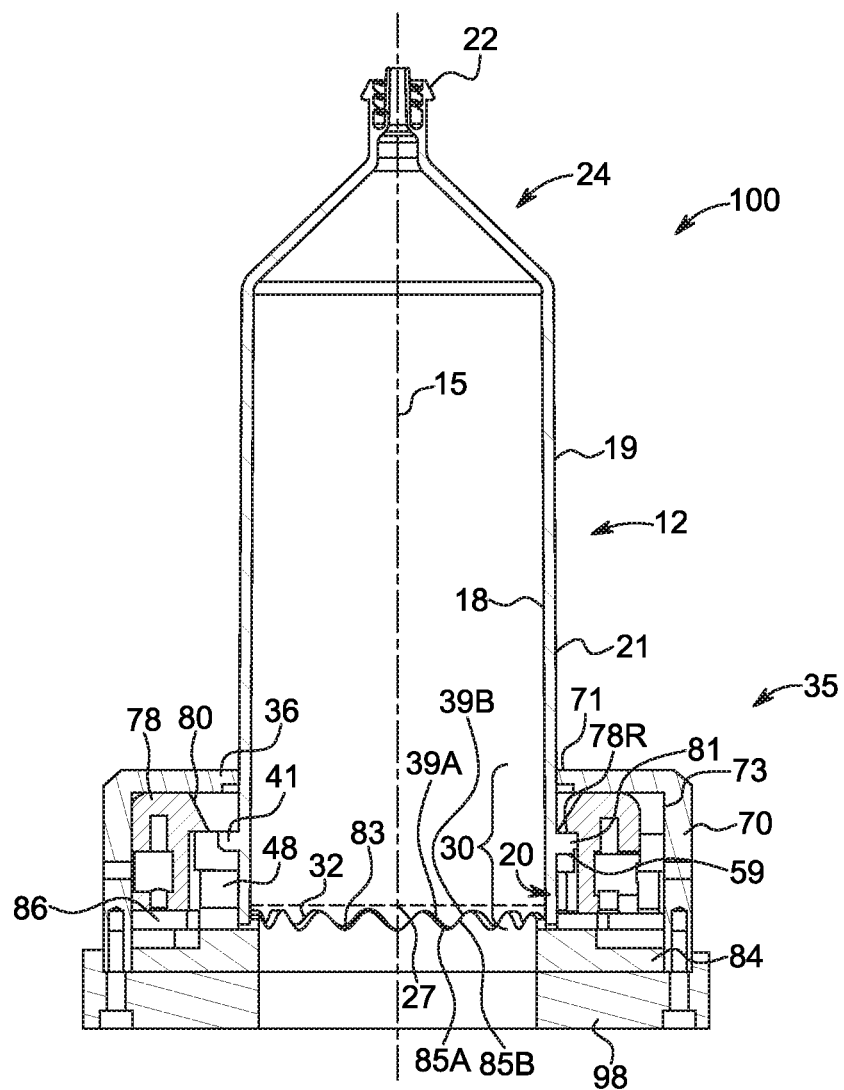
FIG. 2B is a cross-sectional assembled view of the connection interface shown in FIG. 2A.

With specific reference to FIGS. 2A-2B, a connection interface 100 for loading and removing/ejecting the at least one syringe 12 from the at least one syringe port 16 of the injector 10 (shown in FIG. 1) is shown in accordance with one embodiment. The syringe 12 and the injector 10 include the connection interface 100 having at least one engagement member 32 provided on the syringe 12 and a corresponding locking mechanism 35 provided on the syringe port 16 of the injector 10 (shown in FIG. 1). In one embodiment, the at least one engagement member 32 is provided on the proximal end 20 of the syringe barrel 18. For example, the at least one engagement member 32 may protrude axially in a proximal direction from the terminal end 27 of the syringe barrel 18. The at least one engagement member 32 may be formed integrally and monolithically with the barrel 18 or it may be affixed or otherwise secured to the terminal end 27 of the barrel 18 using, for example, a frictional fit and/or an adhesive, or by welding. In other embodiments, the at least one engagement member 32 may be formed on the terminal end 27 of the barrel 18 by etching, laser cutting, machining, or molding. In some embodiments, the one or more engagement members 32 cooperate with at least a portion of the locking mechanism to self-orient the syringe 12 relative to the syringe port 16 such that the syringe 12 may be releasably locked with the syringe port 16 without physical aligning of the syringe or other effort by the user or technician to orient the syringe 12 with syringe port 16 and/or locking mechanism 35.

In the embodiment shown in FIGS. 2A-2B, the at least one engagement member 32 is formed as one or more projections that protrude axially in a proximal direction from the terminal end 27 of the syringe barrel 18 indicated by a dashed line in FIGS. 1B and 2A-2B. The at least one engagement member 32 may have the same radial thickness as the sidewall 19 of the syringe barrel 18 such that the at least one engagement member 32 is substantially continuous with the outer surface 21 and the inner surface 23 (shown in FIG. 1B) of the barrel 18. In other embodiments, the at least one engagement member 32 may protrude radially outward or radially inward relative to the outer surface 21 of the barrel 18. In addition, or alternatively, the at least one engagement member 32 may protrude radially outward or radially inward relative to the inner surface 23 of the barrel 18. In other embodiments, the at least one engagement members 32 may be located within the interior of sidewall 19, for example, such that terminal ends of the inner surface 23 and outer surface 21 are substantially even with the proximal end of the at least one engagement member 32. In certain embodiments, a plurality of engagement members 32 may be arranged around a circumference of the barrel 18 in a waveform or sinusoidal form, as detailed herein. In embodiments where more than two engagement members 32 are provided, the engagement member 32 may be evenly spaced about an outer circumference of the barrel 18. For example, in an embodiment with six engagement members 32, each engagement member 32 is separated 60 degrees apart from adjacent engagement members 32. In other embodiments having x engagement members 32, each engagement member 32 is separated 360/x degrees apart from adjacent engagement members 32, where x is an integer from 1 to 360. In other embodiments, the at least one engagement members 32 may have unequal angular spacing therebetween about the outer circumference of the barrel 18. For example, one or more engagement members 32 may subtend an angle A (shown in FIG. 1B), which may be more than 60 degrees or less than 60 degrees of the circumference of the barrel 18. In some embodiments, where the at least one engagement members 32 have unequal angular spacing, the spacing and arrangement of the various engagement members 32 may be used to encode information regarding the syringe and/or the syringe content, such as manufacturer, lot number, date of manufacture, volume, pressure minimum/maximum, compatibility with various medical fluids, etc. In some embodiments, each of the engagement members 32 may protrude at an equal distance from the terminal end 27 of the syringe barrel 18 in a proximal direction. In other embodiments, one or more engagement members 32 may be longer or shorter than the remaining engagement members 32. Each engagement member 32 is substantially rigid and free from deflecting in a radial or circumferential direction during insertion and removal of the syringe 12 to and from the syringe port 16. Each engagement member 32 may be continuous and uninterrupted, or it may be comprised of a plurality of separate elements that together define the engagement member 32.

Referring back to FIG. 1B, each of the engagement members 32 may have a substantially pointed proximal end 37 with a pair of tapered surfaces 39A-39B that extend from the proximal end 37 of engagement member 32 in a distal direction along the longitudinal axis 15 toward the terminal end 27 of the syringe 12. The proximal end 37 may have a sharp or rounded point. At least one of the tapered surfaces 39A-39B may be angled axially and/or circumferentially relative to a direction of the longitudinal axis 15 at an angle B (shown in FIG. 1B). The axial/circumferential tapering of the at least one tapered surfaces 39A-39B relative to the longitudinal axis 15 may be defined as an angle of inclination of at least one of the tapered surfaces 39A-39B in a cylindrical plan projection view in a direction from the distal end 24 toward the proximal end 20 of the syringe barrel 18. The tapered surfaces 39A-39B may be angled at a same or different angle relative to the longitudinal axis 15. In some embodiments, the tapered surfaces 39A-39B may be linear, curved, or a combination thereof. In other embodiments, the profile of one of the tapered surfaces 39A-39B may the same or different from the other of the tapered surfaces 39A-39B. For example, one of the tapered surfaces 39A-39B may be angled relative to the direction of the longitudinal axis 15, while the other of the tapered surfaces 39A-39B may be parallel with the direction of the longitudinal axis 15. In embodiments where at least two engagement members 32 are positioned adjacent to each other, the tapered surface 39A on one engagement member 32 may transition to the tapered surface 39B of each adjacent engagement member 32.

Figure 4A:
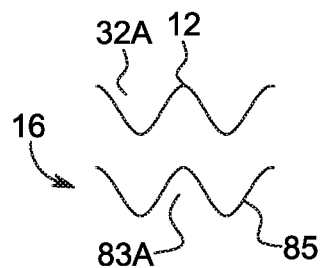
FIGS. 4A-4Q show various embodiments of engagement members on a syringe.

While FIGS. 2A-2B illustrate one non-limiting embodiment of the at least one engagement member 32, various other shapes are also contemplated (see, for example FIG. 4A-4Q for other non-limiting embodiments). For example, the at least one engagement member 32 may have a generally circular, triangular, square, rectangular, or any other polygonal shape. In each embodiment, the at least one engagement member 32, in combination with the retention flange 41, is configured for forming a self-orienting locking engagement with a corresponding locking mechanism 35 in the syringe port 16 of the injector 10 for releasably retaining the syringe 12 in the syringe port 16, as described herein. For each of the embodiments of the engagement member 32, it is also contemplated that the number of engagement members 32 used may be varied while remaining within the scope of the present disclosure. For example, for the syringe 12 illustrated in FIG. 1B, it is contemplated that only one engagement member 32 is provided at the terminal end 27 of the syringe 12. While a single engagement member 32 may be used, embodiments of the syringe 12 may have at least two engagement members 32. In some embodiments having even numbers of engagement members 32, the engagement members 32 may be located diametrically opposite one another. In other embodiments, the engagement members 32 are provided adjacent to each other. The engagement members 32 may be appropriately sized and optionally may be of different circumferential dimension. Various non-limiting embodiments of suitable shapes for the at least one engagement member 32 are described herein with reference to FIGS. 4A-4Q.

With continuing reference to FIGS. 2A-2B, the syringe port 16 of the injector 10 has a locking mechanism 35 configured to operatively engage the at least one engagement member 32 and the retention flange 41 of the syringe 12. The locking mechanism 35 includes a housing 70 with a central opening 71 configured to receive the proximal end 20 of the syringe 12. The housing 70 may be formed as part of the housing 14 of the injector 10 (shown in FIG. 1A) or may be attachable to the housing 14 to convert an existing injector to include the presently described locking mechanism 35. A guide ring 48 may be secured relative to the housing 70 such the guide ring 48 cannot rotate or move longitudinally relative to the housing 70. In one embodiment, the guide ring 48 has a body 72 having one or more tabs 74 (shown in FIG. 2A) extending radially outward from an outer circumference of the body 72. The body 72 of the guide ring 48 may have a continuous annular shape, or it may be formed from two or more discrete segments. When installed within the housing 70, the one or more tabs 74 engage corresponding one or more grooves 76 (shown in FIG. 2A) on an inner sidewall 73 of the housing 70 to prevent rotation/longitudinal movement of guide ring 48. In other embodiments, the guide ring 48 may be secured to the housing 70 by other mechanical fastening arrangements, such as a clip, fastener, or a snap fit arrangement. In further embodiments, the guide ring 48 may be welded, glued, or molded with the housing 70. When installed on the housing 70, a central axis of the guide ring 48 is coaxial with a central axis of the housing 70.

With reference to FIG. 2A, the guide ring 48 has one or more first recesses 60 that are configured to slidably receive a corresponding one or more deflectable retaining elements 78. The one or more first recesses 60 may be evenly spaced about the body 72 of the guide ring 48. In one embodiment, the one or more first recesses 60 extend from an inner circumference of the guide ring 48 to an outer circumference thereof. For example, in an embodiment where the guide ring 48 has four first recesses 60, each first recess 60 may be separated 90 degrees apart from the first recesses 60 adjacent on either side. In other embodiments, the one or more first recesses 60 may be unevenly spaced about the body 72 of the guide ring 48. The number of first recesses 60 on the guide ring 48 may correspond to the number of deflectable retaining elements 78. First recesses 60 may include a groove or pin on the bottom surface to interface with a pin or groove, respectively, on the bottom surface of deflectable retaining elements 78 to guide movement of the deflectable retaining elements 78. The lateral edges of each first recess 60 define a radial travel path for guiding the movement of the deflectable retaining elements 78 in a radial direction as the insertion portion 30 of the syringe 12 is inserted into and out of the guide ring 48. At least a portion of a top surface of the guide ring 48 may define a stop surface 59 that limits a movement of the syringe 12 in the proximal direction when the syringe 12 is inserted into the locking mechanism 35. In one embodiment, the retention flange 41 of the syringe 12 engages the stop surface 59 to limit the movement of the syringe 12 in the proximal direction.

With continued reference to FIG. 2A, the locking mechanism 35 further includes one or more deflectable retaining elements 78 configured for sliding in a radial direction relative to the guide ring 48. As detailed further herein, each of the one or more deflectable retaining elements 78 is radially slidable relative to the guide ring 48 and the housing 70, which are both fixed relative to each other. At least one first elastically resilient member 102 (shown in FIG. 2A), such as a spring, is connected at one end to at least a portion of the one or more deflectable retaining elements 78 and at the other end to at least a portion of the housing 70. The at least one first elastically resilient member 102 urges the one or more deflectable retaining elements 78 to a first position (see FIG. 2B) where a locking lip 80 on the at least one deflectable retaining element 78 is positioned over the stop surface 59 of the guide ring 48 to define a retaining gap 81 (see FIG. 2B). In one embodiment, by inserting the syringe 12 into the syringe port 16, the retention flange 41 of the syringe 12 engages the locking lip 80 of the at least one deflectable retaining element 78 to deflect the deflectable retaining element 78 radially outward and allow the syringe 12 to be inserted into the locking mechanism 35. The locking lip 80 may be radially angled relative to the longitudinal axis 15 such that movement of the syringe 12 in the proximal direction results in a force having a radially directed component that urges the at least one deflectable retaining element 78 radially outward relative to the syringe 12. Alternatively, the proximal surface of the retention flange 41 may be radially angled or beveled relative to the longitudinal axis 15 such that movement of the syringe 12 in the proximal direction results in a force having a radially directed component that urges the at least one deflectable retaining element 78 radially outward relative to the syringe 12. After the retention flange 41 of the syringe 12 clears the locking lip 80, the at least one deflectable retaining element 78 is restored to its initial, first position under the urging of the at least one first elastically resilient member 102. In order to release the syringe 12 from the locking mechanism 35, the one or more engagement members 32 on the syringe 12 engage a lock/release ring 84, and, when rotated, cause the one or more deflectable retaining elements 78 to move to a second or open position and allowing ejection of the syringe 12 from the locking mechanism 35, as described herein.

With continued reference to FIG. 2A, the locking mechanism 35 may further include the lock/release ring 84 having a generally annular shape. The lock/release ring 84 is configured for engaging one or more of the at least one engagement member 32 to control selective positioning of the syringe 12 within the syringe port 16 to allow for selective locking engagement of one or more deflectable retaining elements 78 with the retention flange 41 of the syringe 12. The lock/release ring 84 is rotatable relative to the housing 70 with the rotation of the syringe 12 about its longitudinal axis 15 by engagement of the at least one engagement member 32 with at least one syringe engagement member 83.

In certain embodiments, the lock/release ring 84 has one or more syringe engagement members 83 extending around an inner circumference of the lock/release ring 84. The one or more syringe engagement members 83 have a complementary shape to that of one or more of the at least one engagement members 32 on the syringe 12. In one embodiment, the one or more syringe engagement members 83 are shaped to correspond to the shape of the at least one engagement members 32 at the terminal end 27 of the syringe 12. For example, in various embodiments, the one or more one or more syringe engagement members 83 may have a waveform or sinusoidal shape. The one or more syringe engagement members 83 have interacting surfaces 85A, 85B along which the tapered surfaces 39A-39B can slide as the syringe 12 is inserted into or withdrawn from the syringe port 16. The interacting surfaces 85A, 85B are tapered to a sharp or rounded point in a distal direction facing the syringe 12. At least one of the interacting surfaces 85A, 85B may be angled axially relative to a direction of the longitudinal axis 15. The axial tapering of the at least one interacting surface 85A, 85B relative to the longitudinal axis 15 may be defined as an angle of inclination of the interacting surface 85A, 85B in a cylindrical plan projection view in a direction toward the proximal end 20 of the syringe 12 when the syringe 12 is inserted into the syringe port 16. The interacting surfaces 85A, 85B may be angled at a same or different angle relative to the longitudinal axis 15. In some embodiments, the interacting surfaces 85A, 85B may be linear, curved, stepped but defining a substantially linear/curved surface, or a combination thereof. In other embodiments, the profile of one of the interacting surfaces 85A, 85B may the same or different from the other of the interacting surfaces 85A, 85B. For example, one of the interacting surface 85A, 85B may be angled relative to the direction of the longitudinal axis 15, while the other of the interacting surface 85A, 85B may be parallel with the direction of the longitudinal axis 15.

In embodiments where more than two engagement members 32 are provided on the syringe 12, the one or more syringe engagement members 83 may be shaped to have a corresponding or complimentary shape and angular spacing such that each of the engagement members 32 engages a respective syringe engagement member 83. In other embodiments, the at least one engagement members 32 may have a multiple of engagement members 32 relative to the number of the one or more syringe engagement members 83. In a first position, such as when the syringe 12 is locked within the locking mechanism 35, each engagement member 32 is aligned with the corresponding syringe engagement member 83. In a second position, such as when the syringe 12 is to be removed from the locking mechanism 35, each engagement member 32 is rotationally moved out of alignment with the corresponding syringe engagement member 83.

With continuing reference to FIG. 2A, the lock/release ring 84 further includes a guide slot 86 to guide the movement of each of the deflectable retaining elements 78. Each guide slot 86 is disposed on an outer periphery of a top surface 88 of the lock/release ring 84. Each guide slot 86 has a guide track 90 on which the corresponding deflectable retaining element 78 is guided between the first position, where the syringe 12 is locked within the locking mechanism 35, and a second position, where the syringe 12 is unlocked from the locking mechanism 35. In one embodiment, at least a portion of each deflectable retaining element 78 engages the guide track 90, such as by a pin or other engaging member protruding proximally from the bottom of the deflectable retaining element 78. In a first position, each deflectable retaining element 78 engages the guide track 90 at a first end 92 such that each deflectable retaining element 78 is at its most radially-inward position. In this position, the retention flange 41 of the syringe 12 is retained by the locking lip 80 of the one or more deflectable retaining elements 78 such that the syringe 12 cannot be removed from the locking mechanism 35 without rotating the syringe 12 relative to its longitudinal axis 15 and engaging the release mechanism. With the rotation of the syringe 12 about its longitudinal axis 15, the lock/release ring 84 is rotated such that each deflectable retaining element 78 is guided radially outward along the guide track 90 toward a second end 94, where each deflectable retaining element 78 is at its most radially-outward position. In this position, the syringe 12 is removed from the locking mechanism 35 by ejecting or urging the syringe 12 in a distal direction such that the retention flange 41 clears the locking lip 80 of each deflectable retaining element 78. As the syringe 12 is released from the locking mechanism 35, the lock/release ring 84 is concurrently rotated to the first position under a restoring action of a second elastically resilient member 96 that may be secured to a base 98 of the housing 70. In certain embodiments, rotation of the lock/release ring 84 back to the first position under the restoring action of a second elastically resilient member 96 may provide a lateral force to the syringe 12 to eject or urge the syringe 12 out of the syringe port 16.

To insert the syringe 12 into the syringe port 16, the longitudinal axis 15 of the syringe 12 is roughly aligned with the longitudinal axis of the syringe port 16. Initially, the syringe 12 can be inserted into a top portion of the central opening 71 without rotationally orienting the syringe 12 about the longitudinal axis 15 relative to the syringe port 16. The insertion portion 30 of the syringe 12 is inserted into the opening 71 of the syringe port 16. The syringe retention flange 41 is urged in a proximal direction into contact with the locking lip 80 of the at least one deflectable retaining element 78 to deflect it radially outward and allow the syringe 12 to be inserted into the housing 70. Continued proximal movement of the syringe 12 relative the syringe port 16 causes the one or more deflectable retaining elements 78 to be deflected radially outward within the first recesses 60 to a second position in which the size of the central opening is increased to allow the retention flange 41 to pass through. The syringe 12 is advanced proximally into the syringe port 16 such that the one or more tapered surfaces 39A, 39B on each engagement member 32 come into contact with the corresponding interacting surfaces 85A, 85B to rotationally self-orient the syringe 12 such that the peaks of the engagement members 32 are received in the valleys of the syringe engagement member 83 on the syringe port 16 and/or until the retention flange 41 engages the stop surface 59 on the guide ring 48. Under the restoring action of the at least one first elastically resilient member 102, the one or more deflectable retaining elements 78 are then urged radially from the second position to the first position where the locking lip 80 of the one or more deflectable retaining elements 78 may be positioned over the retention flange 41 between the stop surface 59 and a bottom face of the locking lip 80. In certain embodiments, wherein the drip flange 36 acts as a retention flange 41 the one or more deflectable retaining elements 78 may be positioned over the retention flange 41 to retain the drip flange 36 between the stop surface 59 and a bottom face of the locking lip 80. An audible and/or tactile feedback may be provided by this action to indicate to the user that the syringe 12 is locked within the syringe port 16.

To unlock and release the syringe 12 from the syringe port 16, the syringe 12 may be rotated about its longitudinal axis 15, for example in a clockwise or counterclockwise direction. Rotation of the syringe 12 causes the at least one engagement members 32 to move against the one or more syringe engagement members 83, thus rotating lock/release ring 84 to move the one or more deflectable retaining elements 78 radially to the second position to release the retention flange 41 from locking lip 80. Continued rotation of syringe 12 causes further movement of the at least one engagement members 32 against and thus axially out of alignment with the one or more syringe engagement members 83 due to an axially directed force component imparted on the syringe 12 by the movement of the tapered surfaces 39A-39B along the interacting tapered surfaces 85A-85B of the syringe engagement members 83. In this manner, the terminal end 27 of the syringe 12 is urged/ejected in a distal direction by movement of the tapered surfaces 39A-39B along the interacting tapered surfaces 85A-85B of one or more syringe engagement members 83. As described herein, as the syringe 12 is rotated, the lock/release ring 84 is also rotated such that each deflectable retaining element 78 is guided radially outward along the guide track 90 toward the second end 94, where each deflectable retaining element 78 is at its most radially-outward position. In this position, due to the axially directed force created by the interaction of the tapered surfaces 39A-39B and the interacting tapered surfaces 85A-85B of the syringe engagement members 83, the syringe barrel 18 and the retaining ring 41 are urged distally against the one or more deflectable retaining elements 78 which further urges the one or more deflectable retaining elements 78 radially outward from a first position to a second position. The syringe 12 may be ejected, urged, or popped out of the syringe port 16 when the locking lip 80 of the one or more deflectable retaining elements 78 clears the retention flange 41 of the syringe 12 without any applied distal force from the user. This tactile and physical confirmation of sufficient rotation for unlocking and the ejection or popping out of the syringe 12 with no further user effort, such as no need for an axial pull, is a significant improvement over prior art syringes and syringe injector ports. The ejected syringe 12 can be readily removed from the locking mechanism 35 by withdrawing the syringe 12 in a distal direction. As the syringe 12 is ejected from the locking mechanism 35, such as when the retaining ring 41 moves distally past locking lip 80 and/or the at least one engagement members 32 disengages from the one or more syringe engagement members 83, the lock/release ring 84 is rotated to the first position under a restoring action of the second elastically resilient member 96 such that the one or more deflectable retaining elements 78 are returned to their first, initial position and the locking mechanism 35 is ready for insertion of a new syringe 12.

To further discuss the operation of the locking mechanism 35, the retention surfaces of the syringe 12 and the syringe port 16 that cooperate to retain the syringe 12 in the syringe port 16 once it is engaged are one or more surfaces of the retention flange 41 on the syringe 12 and the one or more retention surfaces of the deflectable retaining elements 78 on the syringe port 16. The syringe 12 is initially generally axially aligned and inserted into the opening 71 of the syringe port 16. Once partially inserted, the guiding surfaces of the syringe 12 and syringe port 16 that cooperate to self-orient or automatically force the rotational movement to self-orient the syringe 12 and the syringe port 16 for installation are the one or more surfaces 39A-39B of the engagement members 32 on the syringe 12 and the one or more tapered guiding surfaces 85A-85B of syringe engagement member 83 of the syringe port 16. The opening surfaces of the syringe 12 and syringe port 16 that cooperate to push open the syringe port 16 for the installation of the syringe 12 are the one or more bottom surfaces of the retention flange 41 on the syringe 12 and one or more of tapered surfaces of the locking lip 80 on the syringe port 16. The tightening surfaces of the syringe 12 and syringe port 16 that cooperate to take up the mechanical slack or tolerance may include one or more surfaces on the drip flange 36 on the syringe 12 which push against the outside housing or a seal of the syringe port 16 and urge the retention flange 41 against the locking lip 80 on the syringe port 16. Alternatively, the tightening force to urge the syringe 12 forward may be provided by a resilient member, such as a second elastically resilient member 96 that rotationally urges lock/release ring 84 causing a distal force from interaction of one or more surfaces 39A-39B of the engagement members 32 on the syringe 12 and the one or more tapered guiding surfaces 85A-85B of syringe engagement member 83 or a third resilient member (not shown) that urges the lock/release ring 84 in a distal direction, and when cooperating with a syringe 12 of sufficient length, urges the retention flange 41 against the locking lip 80. The detachment surfaces of the syringe 12 and syringe port 16 that cooperate to disengage or remove the syringe 12 from the syringe port 16 are surfaces of the engagement members 32 of the syringe 12 and surfaces of the syringe engagement member 83 of the syringe port 16. The ejection surfaces of the syringe 12 and syringe port 16 that cooperate to create a distally directed force to urge ejection of the syringe 12 from the syringe port 16 are the one or more tapered surfaces 39A, 39B on the engagement members 32 of the syringe 16 and one or more tapered guiding surfaces 85A-85B of the syringe engagement member 83 on the syringe port 16. The rotational stop surfaces of the syringe 12 and syringe port 16 that cooperate to prevent rotation as a luer connector is screwed onto the syringe 12 are one or more tapered surfaces 39A, 39B on the engagement members 32 of the syringe 12 and one or more tapered guiding surfaces 85A-85B of the syringe engagement member 83 on the syringe port 16, as well as any frictional force between the one or more surfaces of the retention flange 41 of the syringe 12 and one or more retention surfaces of the deflectable retaining elements 78 of the syringe port 16 and/or between the bottom surface of drip flange 36 and the outside housing or a seal of the syringe port 16.

Figure 3A:
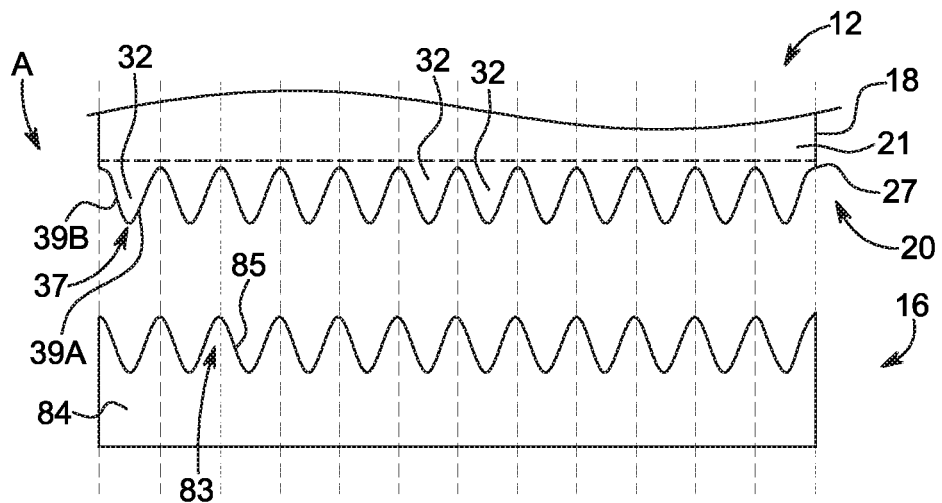
FIGS. 3A-3D show cylindrical plan projection views of engagement members for guiding/ejecting a syringe into/from a fluid injector according to various other embodiments.

FIGS. 3A-3D show cylindrical plan projection views of various embodiments of the at least one engagement members 32 at the proximal end 20 of the syringe 12 and the syringe engagement member 83 of a corresponding syringe port 16 for receiving the proximal end 20 of the syringe 12. With reference to FIG. 3A, a cylindrical plan projection view of the interface between the at least one engagement members 32 at the proximal end 20 of the syringe 12 and the syringe engagement member 83 of the lock/release ring 84 is shown in a rotationally aligned orientation for mating the syringe 12 to the syringe port 16. In this example embodiment, the at least one engagement members 32 on the syringe 12 and the corresponding syringe engagement members 83 on the syringe port 16 are configured as generally sinusoidal projections the proximal end 20 of the syringe 12 having alternating peaks and valleys on the syringe 12 and on the lock/release ring 84. The engagement members 32 on the syringe 12 project axially away from the terminal end 27 of the syringe 12. If the syringe 12 and the syringe engagement members 83 are initially misaligned, the downward or distal force in a direction of arrow A causes a sliding interaction of the tapered surfaces 39A-39B on the syringe 12 with the corresponding tapered guiding surfaces 85A-85B on the syringe engagement members 83. Such sliding interaction causes the syringe 12 to rotate and self-orient into the correct rotational position for alignment with the corresponding tapered guiding surfaces 85A-85B on the syringe engagement members 83 and correctly oriented installation of the syringe 12 into the syringe port 16.

Figure 3B:
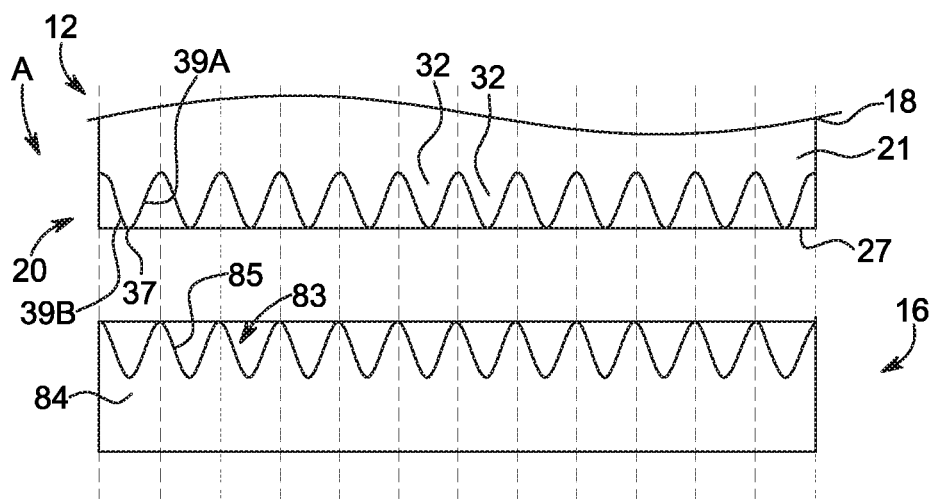
Figure 3C:
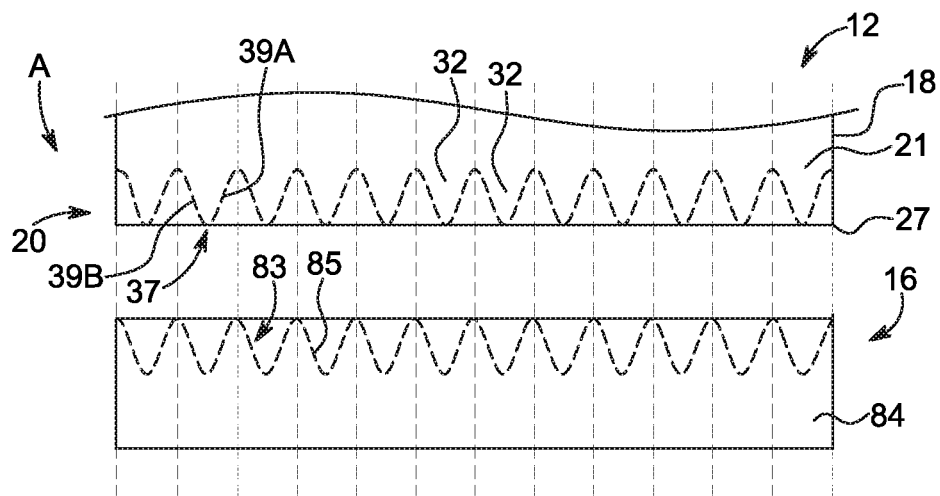

FIG. 3B is another cylindrical plan projection view of an alternative embodiment of the syringe 12. In this embodiment, the engagement members 32 extend only partially through the thickness of sidewall 19 of the syringe barrel 18. In some embodiments, the engagement members 32 may be positioned on the outside surface 21 of the syringe barrel 18. The proximal end 37 of the engagement members 32 may terminate at the terminal end 27 of the syringe barrel 18. In other embodiments, the proximal end 37 may extend in a proximal direction relative to the terminal end 27 of the syringe barrel 19, as illustrated, for example, in FIG. 3A. In this manner, the syringe barrel 18 can be made stronger for a more rigid axial alignment. Additionally, the interior surface of the proximal end 20 may be formed as a smooth continuous surface for an easier installation of the syringe plunger 26. Similarly, the lock/release ring 84 may have syringe engagement members 83 that extend only through a portion of the radial thickness of the lock/release ring 84. FIG. 3C is another cylindrical plan projection view of an alternative embodiment in which the engagement members 32 extend only partially through the thickness of sidewall 19 of the syringe barrel 18 and are positioned on the inside surface of the syringe barrel 12. A corresponding complementary arrangement of the syringe engagement members 83 is present on the lock/release ring 84. In this embodiment, the inside material of the lock/release ring 84 may strengthen the proximal end 20 of the syringe barrel 18 and allow use in higher pressure injections. In some embodiments, the engagement members 32 may extend through at least a portion of the sidewall 19 of the syringe barrel 18 from the outer surface 21 or the inner surface 23 of the syringe 12. In other embodiments, the engagement members 32 are formed by creating voids or pockets of appropriate cross sections within the sidewall 19 of the syringe barrel 18. The voids or pockets may be configured to interact with complementary syringe engagement members 83 present on the lock/release ring 84.

Figure 3D:
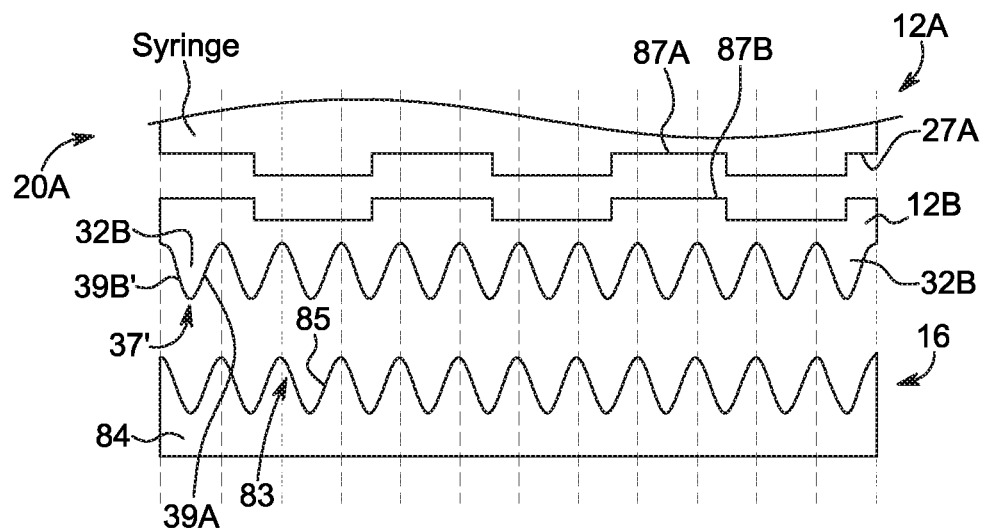

FIG. 3D is a cylindrical plan projection view of an embodiment of an adapter 12B for use with an alternative syringe 12A that cannot itself directly interface with the syringe port 16 and/or locking mechanism 35 described herein. According to an embodiment, the adapter 12B may be configured, for example as a ring, arc, or other shape, that removably or non-removably attaches to at least a portion of the terminal end 27A of the alternative syringe 12A or that may be inserted into locking mechanism 35 in syringe port 16 to adapt locking mechanism 35 to interact with the alternative syringe 12A. The adapter 12B may have one or more engagement members 32B similar to the at least one engagement members 32 of syringe 12 described herein. Each engagement member 32B may be configured for interacting with a corresponding syringe engagement member 83 of the syringe port 16. The distal side of the adapter 12B may have features or projections that mate with corresponding features or projections of the syringe 12A. For example, the adapter 12B may have locking members 87B that are configured to be received within a corresponding locking member 87A on the syringe 12A, or other locking features that allow syringe 12A to mate with adapter 12B and be retained within syringe port 16 and/or locking mechanism 35.

Figure 4B:
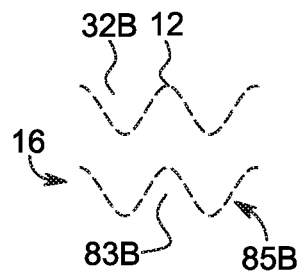
Figure 4C:
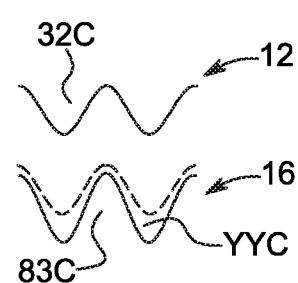
Figure 4D:
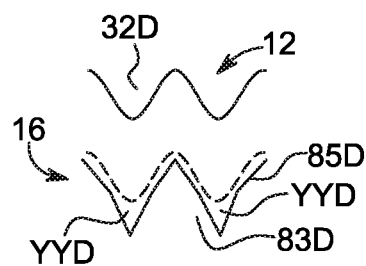
Figure 4E:
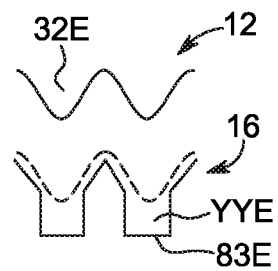
Figure 4F:
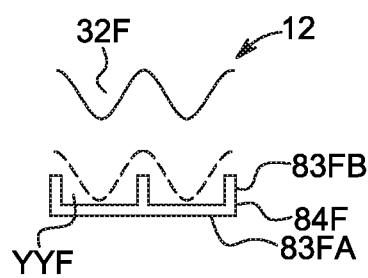
Figure 4G:
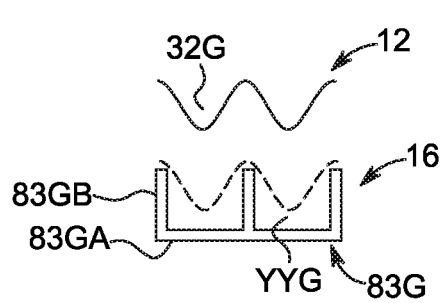
Figure 4H:
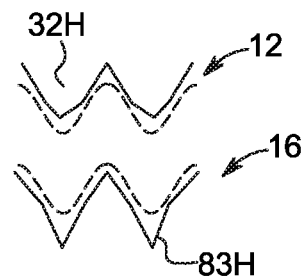
Figure 4I:
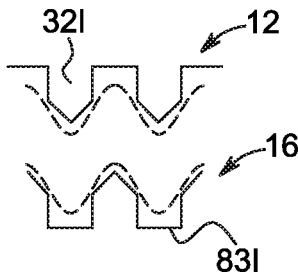

FIGS. 4A-4Q show portions of the cylindrical plan projection views of various embodiments of a portion of the at least one engagement members 32 on the syringe 12 and the corresponding embodiments of syringe engagement members 83 on the lock/release ring 84 in syringe port 16. FIGS. 4A-4Q display shapes of alternative embodiments of engagement members 32 (labeled as 32A-32Q) and/or syringe engagement members 83 (labeled as 83A-83Q) suitable for use with embodiments of the syringe 12 and/or lock/release ring 84 in syringe port 16. FIG. 4A shows segments of engagement members 32 and 83 of the embodiment described herein with reference to FIG. 3A in a cylindrical plan projection view. FIG. 4B illustrates with dotted lines the approximate surfaces of engagement members 32B on the syringe 12 and the corresponding syringe engagement members 83B on the syringe port 16 for various embodiments. FIG. 4C shows an embodiment in which a valley YYC of syringe engagement members 83C is extended compared to the surface of engagement member 32C, while FIG. 4D shows an embodiment in which the surfaces of the syringe engagement member 83D include one or more linear segments to define a valley YYD for receiving engagement member 32D. FIG. 4E illustrates an embodiment in which at least a portion of a valley YYE of 83E has a substantially rectangular profile, for example, to reduce interference from any debris or other external material while still being capable of interacting with engagement member 34E. FIG. 4F illustrates an embodiment in which the syringe engagement member 83F has a flat bottom surface 83FA with one or more distal projections 83FB which may selectively contact the engagement members 32F on the syringe 12. In this embodiment, the bottom segment of engagement members 32F of syringe 12 touch valley sections YYF of the syringe engagement member 83F to allow some rotational slop, gap, or tolerance before rotation of the syringe 12 will cause contact between tapered surface 32F and one or more distal projection 83FB and a corresponding rotation of the lock/release ring 84F. In the embodiment shown in FIG. 4G, the bottom segment of the engagement members 32G do not touch valley sections YYG of the syringe engagement member 83G. Rather, the engagement members 32G engage at least a portion of the projections 83GB in an operation similar to that in FIG. 4F. FIG. 4H shows an embodiment in which both the engagement members 32H and the syringe engagement members 83H have at least one segmented linear surface, with the peaks of the syringe engagement members 83H fitting into but preferably not fully filling the valleys of engagement members 32H on the syringe 12. FIG. 4I shows another embodiment in which both the engagement members 32I and syringe engagement members 83I are too wide to fit completely into the respective valleys to ensure that the interaction takes place between the angled surfaces of the respective members.

FIG. 4J shows engagement members 32J having a plurality of separate segments of varying length in the longitudinal direction 15, with the tips or ends of the segments defining the generally sinusoidal profile or other profile described herein required to fit within syringe engagement members 83J. FIG. 4K shows engagement members 32K having a plurality of separate segments of a common length such that a portion of the segments may flex radially but not circumferentially when the syringe 12 is inserted into the syringe port 16. In this embodiment, when the engagement members 32K interact with the syringe engagement members 83K, the overlapping projections flex radially relative to syringe engagement members 83K whereas the non-overlapping projections on engagement members 32K engage the corresponding syringe engagement members 83K as described herein. In an alternative embodiment, syringe engagement members 83 may include spring-loaded balls or fingers which can travel circumferentially and group together to match the contours of engagement members 32 on the syringe 12 and transmit rotational forces for activation of the disengagement action. FIG. 4L shows an embodiment with engagement members 32L having a rod-shaped structure including a projection substantially parallel with the longitudinal axis 15 configured for interacting with the syringe engagement member 83L. The engagement members 32L have a virtual tapering surfaces 39A-39B extending from a proximal tip of each engagement member 32L in a distal direction toward the terminal end 27 of the syringe barrel 18 (shown in FIG. 1B). FIG. 4M shows an embodiment of the engagement members 32M having a rod-shaped structure with a projection that is angled such that it tapers relative to the longitudinal axis 15 (shown in FIG. 2B). In some embodiments, the engagement members 32M may be sufficiently rigid to interact with the syringe engagement member 83M. Other embodiments of engagement member 32 may include a strengthening support between the syringe terminal end 27 and a middle portion of the projection. Alternatively, the engagement members 32M may flex when rotated for disengagement and thus provide and added spring force during the ejection of the syringe 12 from the syringe port 16.

FIG. 4N shows an embodiment in which the engagement members 32N and syringe engagement members 83N define a saw tooth pattern having substantially linear tapered surfaces meeting to form a substantially angled peak. The engagement members 32N may have equal or unequal peak to peak height or taper angles relative to the syringe engagement members 83N or vice versa. FIG. 4O illustrates an embodiment in which the frequency of the engagement members 32O on the syringe 12 is greater than, for example twice, that of the syringe engagement members 83O on the lock/release ring 84 in syringe port 16. In other embodiments, the frequency of the engagement members 32O on the syringe 12 may be an integer multiple to the frequency of the syringe engagement members 83O on the syringe port 16. In other embodiments, the frequency of the engagement members 32O on the syringe 12 may be less than the frequency of the syringe engagement members 83O on the syringe port 16, for example an integer ratio of the frequency. FIG. 4P illustrates an embodiment in which one or more of the syringe engagement members 83P is absent. Although not shown, one or more of the engagement members 32P on the syringe 12 could also be absent. Alternatively, one or more of the engagement members 32P may be absent. FIG. 4Q illustrates an embodiment in which the engagement members 32Q are rounded at their proximal point and angular at their most distal point, with complementary syringe engagement member 83Q having a substantially pointed peak. While various non-embodiments for shapes of the at least one engagement members 32 have been represented in FIG. 4A-4Q it is to be understood that such shapes may be used on the syringe engagement members 83 or on both the engagement members 32 and syringe engagement members 83 according to other embodiments of the present disclosure. Further, combinations of the various engagement member shapes may be used on syringe 12, lock/release ring 84 or both. In addition, the engagement members 32 on a syringe 12 may include various combinations of the various embodiments of the engagement members represented in FIGS. 4A-4Q and equivalents, as described herein. Further, the syringe engagement members 83 on a lock/release ring 84 may include various combinations of the various embodiments of the syringe engagement members represented in FIGS. 4A-4Q and equivalents, as described herein.

Figure 5A:
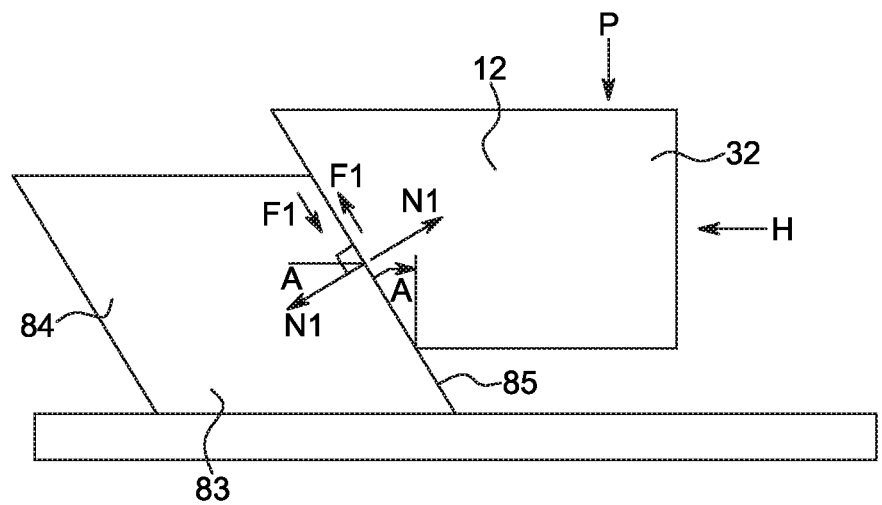
FIG. 5A is a schematic diagram of forces on the connection interface during an insertion of a syringe into a fluid injector.
Figure 5B:
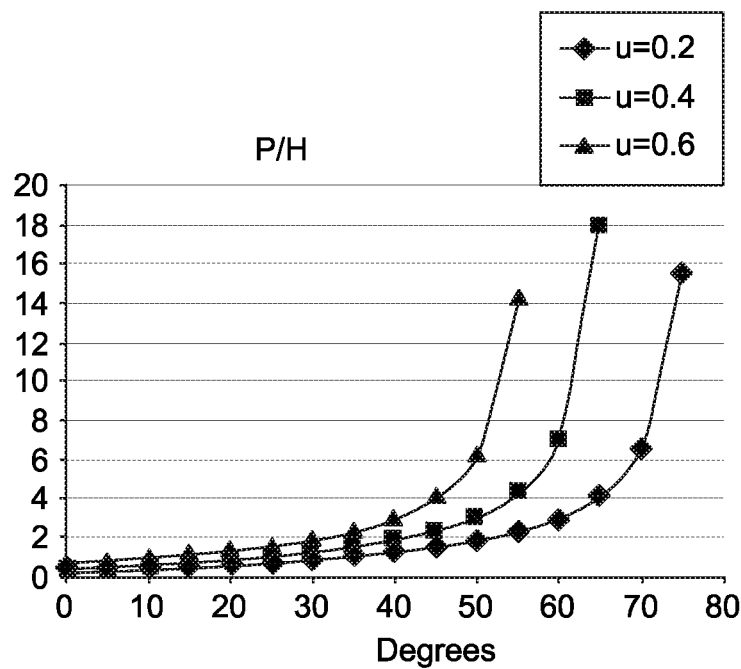
FIG. 5B is a graph of a syringe insertion force as a function of an angle of tapered surfaces at a connection interface for materials with different coefficients of friction μ.

FIG. 5A is an illustration of a generalized free body diagram of forces present between the tapered surface 39A-39B on the at least one engagement member 32 and the tapered guiding surface 85A-85B on the at least one syringe engagement member 83 during insertion of the syringe 12 into the syringe port 16. The at least one engagement member 32 on the syringe 12 interacts with the at least one syringe engagement member 83 on the syringe port 16 due to a distally directed force P provided by the user's hand. Performing a static force analysis on this generalized interaction provides an estimate of the force for insertion as a function of the angle A measured from the axial direction of the interaction of the two sets of tapered surfaces for various coefficients of friction μ between the surfaces, as shown in FIG. 5B. In some embodiments, the syringe 12 may be made from a polyethylene terephthalate (PET) material, while the lock/release ring 84 may be made from a polyoxymethylene (POM) material, such as DELRIN™. The coefficient of friction μ of DELRIN™ on another DELRIN™ surface is approximately 0.4. The coefficients of friction of various other surfaces can be measured and used in the calculations as appropriate. Using this value, a practical limit of the angle A to enable reasonable insertion behavior is approximately 60-65 degrees measured relative to a direction of the longitudinal axis 15 of the syringe 12. Other practical limits of angle A may be determined for other coefficients of friction to determine the optimal angle range for tapered surfaces 39A-39B and 85A-85B of the at least one engagement members 32 and the at least one syringe engagement members 83, respectively. For a coefficient of friction of 0.6, an angle less than 50-55° may be used.

Figure 6A:
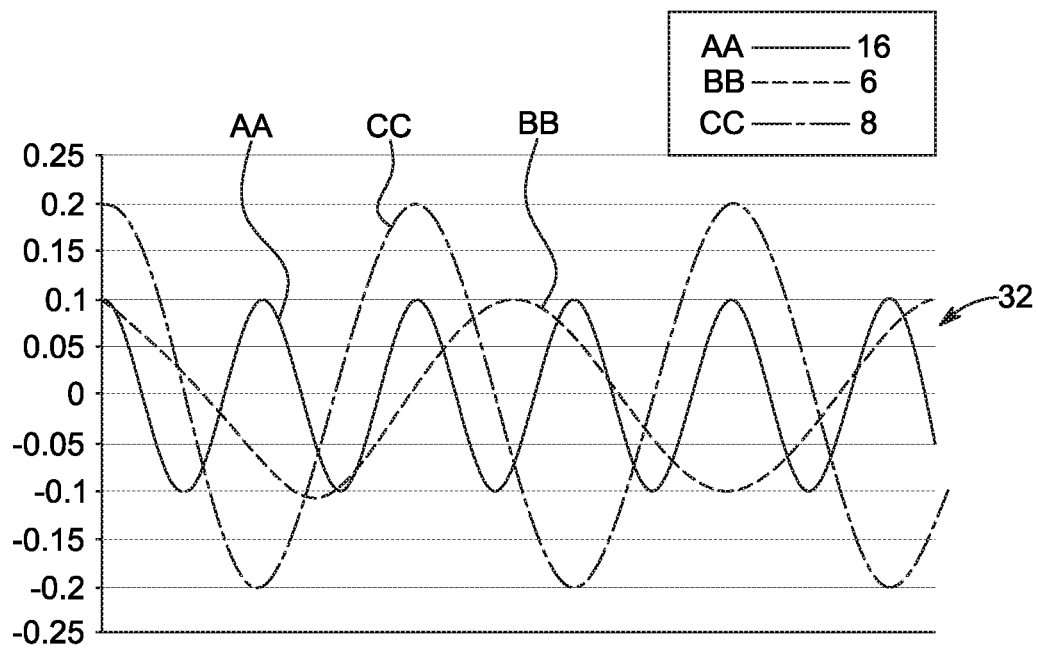
FIG. 6A is a graphical overlay of various profiles of engagement members on a syringe.
Figure 6B:
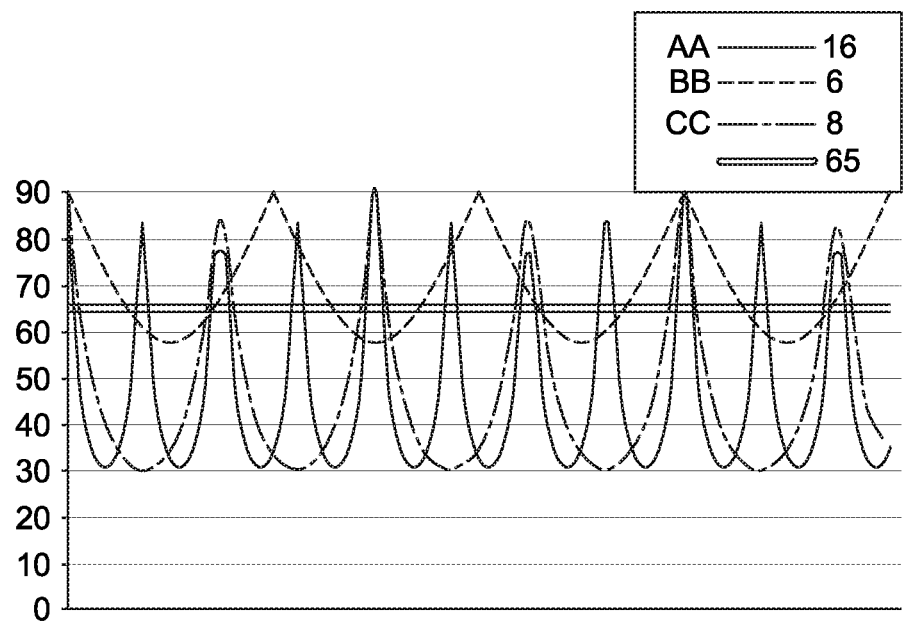
FIG. 6B is a graph of an angular orientation relative to a longitudinal axis of a sinusoidal engagement member about a circumference of a syringe.

FIG. 6A shows an overlay of three different sinusoidal designs for the at least one engagement members 32 of syringe 12. Pattern AA has a peak to peak height of 0.2 inch and a repetition of 16 cycles around a 1.9 inch diameter syringe. The barrel wall thickness is relatively small compared to the syringe diameter. Pattern BB has a peak to peak height of 0.2 inch, and a repetition of 6 cycles around the 1.9 inch diameter syringe. Pattern CC has a peak to peak height of 0.4 inch with a repetition of 8 cycles around a 1.9 inch diameter syringe. FIG. 6B shows the angular orientation relative to the longitudinal axis 15 (shown in FIG. 5A) around a circumference of a 1.9 inch diameter syringe. The angle may be expressed by a formula Angle=90−Abs(ArcTan(−(H*N/D)*Sin(N*theta))), where H is the peak to peak height of the pattern, D is the diameter of the pattern, N is the number of cycles of repetition around the barrel, and the angle is measured from a direction parallel to the orientation of the longitudinal axis 15 shown in FIG. 5A. From this calculation, patterns AA and CC have small portions where the angle is above 65° and thus may be difficult to insert.

Figure 7A:
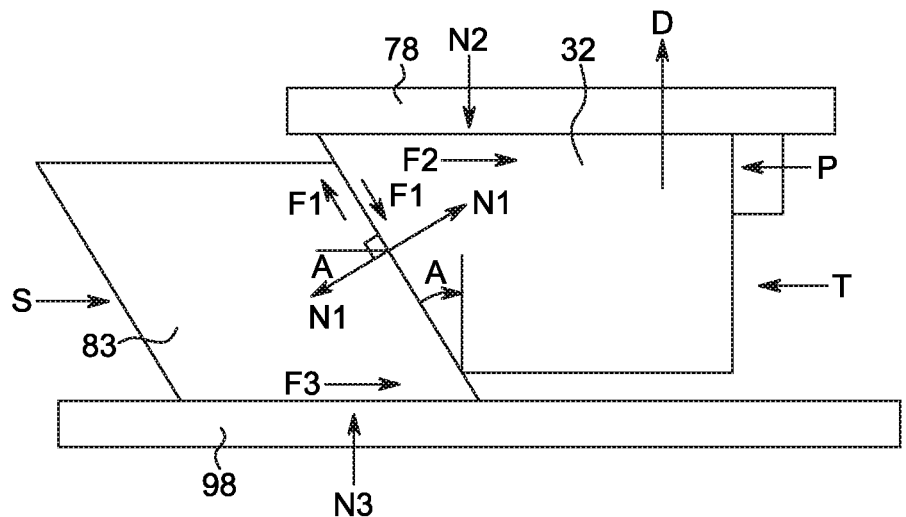
FIG. 7A is a schematic diagram of forces on the connection interface during an ejection of a syringe from a fluid injector.
Figure 7B:
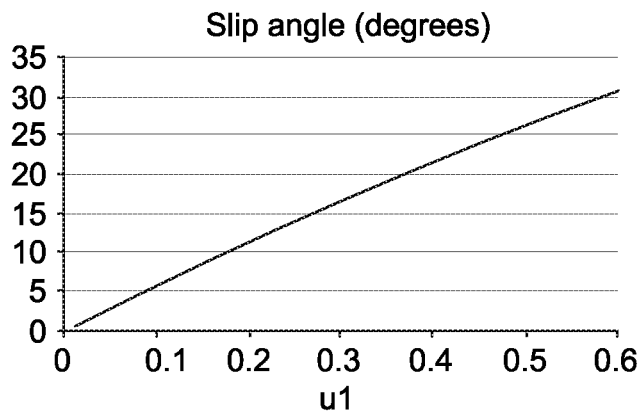
FIG. 7B is a graph of a slip angle for syringe ejection as a function of a coefficient of friction between a syringe and a locking mechanism.
Figure 7C:
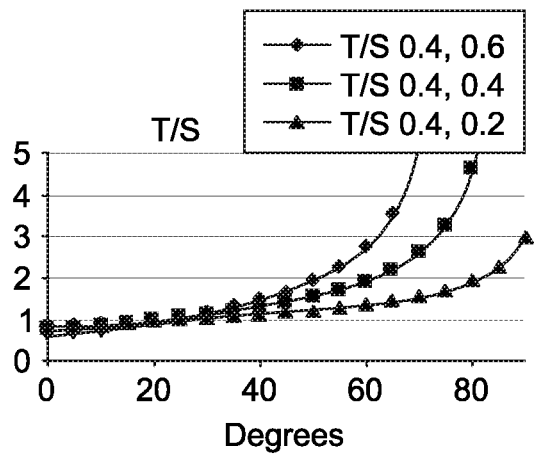
FIG. 7C is a graph of a ratio of a rotational force on a syringe during ejection relative to a restoring force of a locking mechanism as a function of an angle of tapered surfaces at a connection interface.

FIG. 7A is an illustration of a generalized free body diagram of forces between the tapered surface 39A-39B on the at least one engagement member 32 and the tapered guiding surface 85A-85B on the at least one syringe engagement member 83 present during release ejection of the syringe 12 into the syringe port 16. The forces on the syringe 12 are the normal force N1 and frictional force F1 of the engagement member 32 against the engagement member 83, the normal force N2 and frictional force F2 of the deflectable retaining elements 78 on the retention flange 41 as well as the rotational force T applied by the user to rotate the syringe and any force D urging the syringe proximally provided by the drip flange 36, for example. The syringe engagement member 83 there has a normal force N3 and frictional force F3 as it slides over base 98 and the restoring force S from the second elastically resilient members 96. As shown in FIG. 7B, the static analysis shows that the angle A is needed for slip at the interface between engagement member 32 and the syringe engagement member 83. For a coefficient of friction $\mu 1$ of 0.4, the minimum angle is approximately 20 degrees. Thus for angles greater than 20 degrees, there will be slip and upon sufficient motion for the deflectable retaining elements 78 to clear the retention flange 41, the syringe will be ejected from the syringe port 16. FIG. 7C shows a ratio of the rotational force T to rotate the syringe 12 as the restoring force S of the second elastically resilient member 96 increases. The ratio is relatively constant as the angle increases, but the ratio increases dramatically at higher angles. In some examples, an angle of at least 30 degrees and less than approximately 60 degrees may be used.

In another embodiment, the presence or absence of one or more of the at least one engagement members 32 around the circumference of the syringe barrel 18 may be used to convey or encode information about the syringe 12 or the syringe contents (for example with prefilled syringes). For example, such presence or absence of one or more of the at least one engagement members 32 at specific sites around the circumference of the syringe 12 can be sensed by various electronic means, for example, optical sensors, mechanical switches, capacitive sensors, and other means within the syringe port 16 of injector 10. As an example of encoded information that may be represented by the presence or absence of one or more of the at least one engagement members 32, a single code can be indicative of the absence of engagement member 32, the absence of two or more engagement members 32 may provide multiple codes, for example for different spaces between the engagement members 32.

Figure 8A:
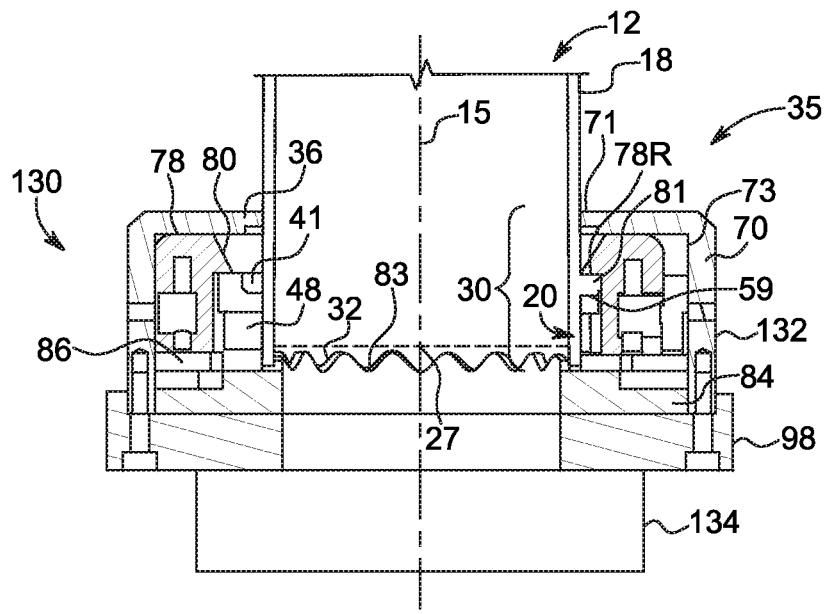
FIG. 8A is a side cross-sectional view of a coupling configured for connecting a syringe of the present disclosure to an injector.

With reference to FIG. 8A, a coupling 130, including a mounting member therefor, can be fabricated to be separate from and attachable to the syringe barrel 18. The coupling 130 can, for example, be configured to accept the syringe 12 having at least one engagement member 32 described herein and to adapt the syringe 12 for use with a fluid injector having a syringe port with a locking mechanism not configured to receive the at least one engagement member 32. For example, the coupling 130 can adapt the syringe 12 for use with the fluid injector described in U.S. Pat. No. 5,383,858 or 6,652,489, or any other fluid injector. In some embodiments, the coupling 130 is releasably connectable to the injector. In other embodiments, the coupling 130 may be inserted into and retained in a locking mechanism of the fluid injector. The coupling 130 may also be releasably connected or attached to the syringe 12 independently of the attachment of the coupling to the injector.

Figure 9A:
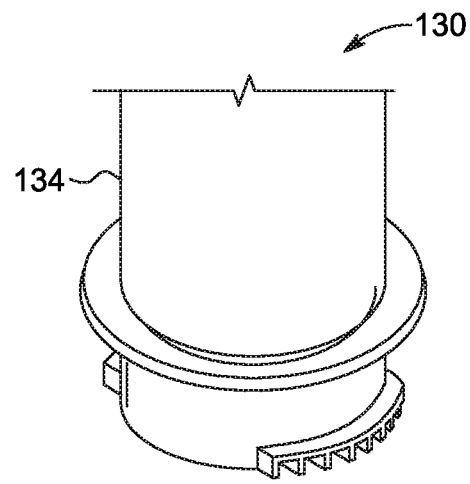
FIGS. 9A-9B are perspective views of alternative embodiments of connection portions of the coupling shown in FIG. 8A.
Figure 9B:
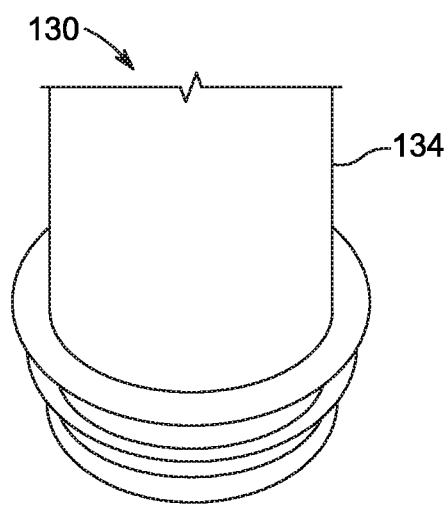

With reference to FIG. 8A, the coupling 130 has a first portion 132 configured for receiving the syringe 12 having at least one engagement member 32 according to an embodiment described herein and a second portion 134 configured for loading into an injector having a syringe port not configured to receive the syringe 12 having at least one engagement member 32 according to an embodiment described herein. The first portion 132 may be directly connected and monolithically formed with the second portion 134. In some embodiments, the first portion 132 may be releasably connected to the second portion 134 such that various second portions (shown in FIGS. 9A-9B) may be used with the first portion 132. With continued reference to FIG. 8A, the first portion 132 has a locking mechanism 35 described herein. In various embodiments, the first portion 132 of the coupling 130 may be configured for releasably receiving the syringe 12 having a corresponding at least one engagement member 32, as described herein. With reference to FIGS. 9A-9B, the second portion 134 of the coupling 130 may have a connection interface configured for connecting with an injector that would otherwise not be capable of receiving the syringe 12 having at least one engagement member 32 described herein. FIG. 9A shows the second portion 134 configured for use with an engagement mechanism of the injector described in U.S. Pat. No. 5,383,858, while FIG. 9B shows the second portion 134 configured for use with an engagement mechanism of the injector described in U.S. Pat. No. 6,652,489. The second portion 134 may be configured to interface with various other injectors not expressly described herein, based on the configuration of the engagement mechanism on the proximal end of the syringe. In some embodiments, the coupling 130 may have a separate mechanism for engaging and disengaging the coupling 130 to and from a locking mechanism of the injector.

Figure 8B:
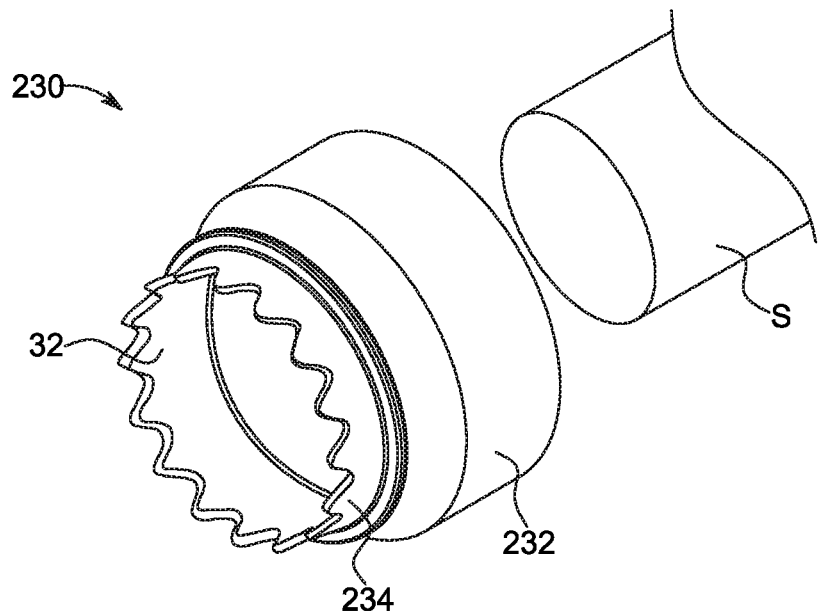
FIG. 8B is a perspective view of an adapter configured for connecting a syringe to an injector of the present disclosure.

With reference to FIG. 8B, an adapter 230 may be configured to receive a syringe S not having one or more engagement members 32 described herein for removably inserting into an injector having the locking mechanism 35 in accordance with one of the embodiments described herein. In various embodiments, the adapter 230 may be configured for connecting to a syringe S for subsequent installation on an injector. For example, the adapter 230 may be connected to the non-compatible syringe S releasably or permanently. Such an adapter 230 may have a connection interface having at least one engagement member 32 in accordance with embodiments described herein. The adapter 230 may be configured for being releasably connectable with an injector having a locking mechanism 35 described herein. The adapter 230 and the syringe S may be connected prior to connecting to the injector, or the adapter 230 may be connected to the injector before the syringe S is connected to the adapter 230. The adapter 230 and syringe S may be removed from the injector after use, with the adapter 230 being disposed of with the syringe S, or being removed from the used syringe S and saved for subsequent use with a different syringe S.

In one embodiment, a first portion 232 of the adapter 230 may be configured for permanently or releasably receiving the syringe S which is not compatible for use with any of the locking mechanisms 35 described herein. In some embodiments, the syringe S may be the syringe described in U.S. Pat. No. 5,383,858 or 6,652,489, or any other syringe type. The adapter 230 allows the non-compatible syringe S to engage and be retained by the locking mechanism 35 described herein. In some embodiments, the adapter 230 may have a separate mechanism for engaging and disengaging the syringe S while the adapter 230 remains connected to the locking mechanism 35 of the injector 10. The first portion 232 may also be a cradle or sleeve to hold or retain other syringes S, for example hand held syringes or syringes having different retention mechanisms or features and allowing them to engage and be retained by locking mechanisms 35. A second portion 234 of the adapter 230 may have at least one engagement member 32 in accordance with embodiments described herein. In some embodiments, the at least one engagement member 32 may have the configuration described herein with reference to FIGS. 1B-4Q. The second portion 234 of the adapter 230 may be configured for being releasably connectable with an injector having a locking mechanism 35 described herein. In this manner, various non-compatible syringes S may be used with an injector having a locking mechanism 35 described herein. In various embodiments, the adapter 230 may be configured for connecting a pressure jacket (not shown) to the injector for use in injection procedures requiring high pressure. For example, the adapter 230 having the pressure jacket may be configured for being releasably connectable with an injector. Such an adapter 230 may have a connection interface having at least one engagement member 32 in accordance with embodiments described herein or alternatively have a connection interface that allows non-compatible syringes to be used with the injector. The adapter 230 may be configured for being releasably, permanently, or semi-permanently connectable with an injector having a locking mechanism 35 described herein and allowing syringes S having alternate retaining mechanisms to be used with the injector. Once connected with the injector, a syringe S may be loaded into the adapter 230 or the pressure jacket attached thereto and be retained therein at its proximal or distal end.

In various embodiments, an adapter 230 may be configured for connecting a syringe having some but not all of the features necessary for subsequent installation into an injector 10 described herein, as described herein with reference to FIG. 3D. The adapter 230 allows a syringe which could not by itself mate or function fully with injector port 16 to mate and at least perform the retention function with the locking mechanism 35. By rotating the adapter 230, the syringe and the adapter may be released from the syringe port. Similarly upon insertion, to the adapter 230 may be pushed proximally for engagement with the syringe. As discussed herein, an adapter can be a ring, such as adapter 12B shown in FIG. 3D which interfaces with the injector port 16 and the syringe 12A. Optionally, the adapter 230 can include additional surfaces (not shown) such as levers, handles, or rings by which the operator can move one or more aspects of the adapter to release the adapter from the syringe port and/or release the syringe from the adapter without having to directly apply a force to or move the syringe.

With reference to FIG. 2A, a system may be provided to transmit information from the syringe 12 to the injector 10 (shown in FIG. 1A). In one embodiment, the syringe 12 may be provided with one or more encoding devices 49 for example, on one or more of the engagement members 32. In other embodiments, the one or more encoding devices 49 may be provided on the outer surface 21 (shown in FIG. 1B), the inner surface 23 (shown in FIG. 1B), within at least a portion of the sidewall 19 (shown in FIG. 1B) of the proximal end 20 of the syringe 12, or on the plunger 26. In some embodiments, the encoding device 49 may be an optically readable member, such as a barcode, while in other embodiments, the encoding device 49 may be an RFID tag, near-field communication device, or any other suitable encoding device. A plurality of encoding devices 49 may be disposed around an inner or outer circumference of the syringe 12 and/or the plunger 26. At least one sensor 51 (shown in FIG. 2A) may be provided on the syringe port 16 to read the encoding device 49. In some embodiments, the at least one sensor 51 may be provided on at least one deflectable retaining element 78. Examples of information which could be encoded on encoding device 49 include, without limitation, dimensions of syringe 12, volume of syringe 12, content of the syringe 12 (in the case of a pre-filled syringe), manufacturing information such as lot numbers, dates and tool cavity number, recommended contrast media flow rates and pressures, and/or loading/injection sequences. In one embodiment, the presence or absence of one or more engagement members 32 may serve as the encoding device. For example, one absent engagement member 32 may represent a first code. Two or more adjacent absent engagement members 32 may represent a second code. Two or more non-adjacent absent engagement members 32 may represent a third code. Various other combinations of present/absent engagement members 32 may represent various other codes. The presence or absence of individual engagement members 32 can be determined by the injector using mechanical switches, electrical material sensors, optically, visually, or by other means know in the sensing art. This syringe encoding information is communicated to the injector control for communication to the operator and for subsequent use in correctly programming and controlling the injector.

In some embodiments, at least a portion of the injector 10 (shown in FIG. 1A), such as the base 98 of the locking mechanism 35 shown in FIGS. 2A and 3A, may have an inner support ring (not shown) that protrudes into at least a portion of the interior volume 25 of the proximal end 20 of the syringe 12. Such a support ring may be removably extendable into at least a portion of the interior volume 25. The support ring may provide radial and axial support to at least a portion of one or more engagement members 32 and/or the inner sidewall 23 (shown in FIG. 1B) of the syringe 12 when the syringe 12 is inserted into the locking mechanism 35. In embodiments where at least one sensor 51 is provided on the syringe port 16, such as shown in FIG. 2A, the support ring may provide a contrasting surface for detecting the presence or absence of the at least one encoding device 49. For example, the support ring may provide a contrasting opaque surface against a translucent or transparent sidewall 19 of the syringe 12 to facilitate the detection of the at least one encoding device 49.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements. For example, it is to be understood that the present disclosure contemplates that, to the extent possible, one or more features of any embodiment can be combined with one or more features of any other embodiment.

We claim:

1. A fluid injector, comprising:
    an injector housing defining at least one syringe port for receiving at least one syringe; and
    a locking mechanism associated with the at least one syringe port for securing at least one syringe within the at least one syringe port, the locking mechanism configured for engaging a retention flange around at least a portion of an outer circumference near the proximal end of the at least one syringe and a plurality of engagement members at the proximal end of the syringe to releasably position and lock the at least one syringe within the at least one syringe port,
    wherein the locking mechanism further comprises a lock/release ring comprising one or more syringe engagement members having a complementary tapered shape for engaging with one or more of the plurality of engagement members when the at least one syringe is inserted into the at least one syringe port, the lock/release ring being rotatable relative to the housing with a rotation of the at least one syringe about the longitudinal axis, wherein rotation of the lock/release ring disengages the locking mechanism from the retention flange on the syringe, allowing the at least one syringe to axially eject from the at least one syringe port, and wherein a taper of each of the plurality of engagement members axially ejects the syringe upon rotation of the syringe.

2. The fluid injector of claim 1, wherein the one or more syringe engagement members comprise a second taper, wherein at least one of the taper of the plurality of engagement members and the second taper rotationally guide the syringe into alignment with the locking mechanism.

3. The fluid injector of claim 2, wherein the lock/release ring is rotatable relative to the injector housing with rotation of the at least one syringe about a longitudinal axis.

4. The fluid injector of claim 3, wherein the one or more syringe engagement members and the plurality of engagement members engage so that rotation of the at least one syringe about the longitudinal axis results in rotation of the lock/release ring.

5. The fluid injector of claim 4, wherein the locking mechanism further comprises at least one deflectable retaining element configured to interact with the retention flange to releasably retain the syringe within the locking mechanism.

6. The fluid injector of claim 5, wherein the at least one deflectable retaining element comprises at least one elastically resilient member connected at one end to at least a portion of the at least of deflectable retaining element, wherein the at least one elastically resilient member urges the at least one deflectable retaining element in a radially inward direction.

7. The fluid injector of claim 5, wherein the at least one deflectable retaining element has a locking lip that is angled relative to a longitudinal axis such that movement of the at least one syringe in a proximal direction causes the at least one deflectable retaining element to move in a radially outward direction.

8. The fluid injector of claim 5, wherein rotation of the lock/release ring from a first position to a second, rotated position causes the at least one deflectable retaining element to move in a radially outward direction.

9. The fluid injector of claim 8, wherein concurrent with the at least one deflectable retaining element moving in the radially outward direction, movement of the taper of the plurality of engagement members relative to the second taper axially ejects the syringe from the locking mechanism.

10. The fluid injector of claim 8, wherein the lock/release ring comprises a second elastically resilient member that rotates the lock/release ring back to the first position.

11. The fluid injector of claim 10, wherein rotation of the lock/release ring back to the first position provides a lateral force to the at least one syringe to further move the taper of the plurality of engagement members relative to the second taper to axially eject the syringe from the locking mechanism.

12. A syringe locking mechanism for a fluid injector, the locking mechanism comprising:
a lock/release ring comprising one or more syringe engagement members having a complementary shape for engaging with one or more of a plurality of engagement members when a syringe is inserted into a syringe port of the fluid injector, the lock/release ring being rotatable relative to a housing of the fluid injector with a rotation of the syringe about a longitudinal axis;
at least one deflectable retaining element configured to interact with a retention flange around at least a portion of an outer circumference near the proximal end of the at least one syringe to releasably retain the syringe within the locking mechanism, wherein the at least one deflectable retaining element has a locking lip that is angled relative to the longitudinal axis such that movement of the at least one syringe in a proximal direction causes the at least one deflectable retaining element to move in a radially outward direction; and
at least one elastically resilient member connected at one end to at least a portion of the at least of deflectable retaining element and at a second end to at least a portion of the fluid injector, wherein the at least one elastically resilient member urges the at least one deflectable retaining element in a radially inward direction.

* * * * *

UNITED STATES PATENT AND TRADEMARK OFFICE
CERTIFICATE OF CORRECTION

PATENT NO. : 11,577,022 B2  
APPLICATION NO. : 16/713335  
DATED : February 14, 2023  
INVENTOR(S) : Cowan et al.

Page 1 of 1

It is certified that error appears in the above-identified patent and that said Letters Patent is hereby corrected as shown below:

In the Specification

In Column 7, Line 32, delete "Lazaro" and insert -- Lazzaro --, therefor.

In Column 10, Line 48, delete "may" and insert -- may be --, therefor.

In Column 13, Line 35, delete "may" and insert -- may be --, therefor.

In Column 14, Line 43, delete "relative" and insert -- relative to --, therefor.

In Column 15, Line 32, delete "retaining ring 41" and insert -- retention flange 41 --, therefor.

In Column 15, Line 48, delete "retaining ring 41" and insert -- retention flange 41 --, therefor.

In Column 16, Line 9, delete "more of" and insert -- more --, therefor.

In Column 23, Line 36, delete "to the" and insert -- the --, therefor.

In Column 24, Line 18, delete "know" and insert -- known --, therefor.

In the Claims

In Column 25, Line 36, in Claim 6, delete "least of" and insert -- least one --, therefor.

In Column 26, Line 39, in Claim 12, delete "least of" and insert -- least one --, therefor.

Signed and Sealed this  
Twenty-fifth Day of July, 2023

Katherine Kelly Vidal  
*Director of the United States Patent and Trademark Office*